(12) United States Patent
Tschirren et al.

(10) Patent No.: US 10,493,212 B2
(45) Date of Patent: Dec. 3, 2019

(54) AUTOINJECTOR HAVING A SETTABLE DOSE

(71) Applicant: TECPHARMA LICENSING AG, Burgdorf (CH)

(72) Inventors: Markus Tschirren, Burgdorf (CH); Christian Schrul, Burgdorf (CH); Jürg Hirschel, Bern (CH)

(73) Assignee: TecPharma Licensing AG, Burgdorf (CH)

( * ) Notice: Subject to any disclaimer, the term of this patent is extended or adjusted under 35 U.S.C. 154(b) by 345 days.

(21) Appl. No.: 15/417,764

(22) Filed: Jan. 27, 2017

(65) Prior Publication Data

US 2017/0136189 A1 May 18, 2017

Related U.S. Application Data

(63) Continuation of application No. PCT/CH2015/000104, filed on Jul. 13, 2015.

(30) Foreign Application Priority Data

Jul. 29, 2014 (CH) ........................................ 1161/14

(51) Int. Cl.
*A61M 5/315* (2006.01)
*A61M 5/20* (2006.01)
(Continued)

(52) U.S. Cl.
CPC ...... *A61M 5/31553* (2013.01); *A61M 5/2033* (2013.01); *A61M 5/3146* (2013.01);
(Continued)

(58) Field of Classification Search
CPC ........ A61M 2005/2013; A61M 5/2033; A61M 5/3146; A61M 5/31501; A61M 5/31536; A61M 5/31553; A61M 5/326
See application file for complete search history.

(56) References Cited

U.S. PATENT DOCUMENTS

2005/0261634 A1* 11/2005 Karlsson ................. A61M 5/20
604/197

FOREIGN PATENT DOCUMENTS

| CH | 707216 A2 | 4/2014 |
|----|-----------|--------|
| EP | 2742962 A2 | 6/2014 |

(Continued)

OTHER PUBLICATIONS

International Preliminary Report on Patentability dated Jan. 31, 2017 for International Application No. PCT/CH2015/00104, 10 pages.

(Continued)

*Primary Examiner* — Deanna K Hall
(74) *Attorney, Agent, or Firm* — Dorsey & Whitney LLP

(57) ABSTRACT

An autoinjector comprises a housing, a product container, a displaceable needle protection sleeve, a plunger rod displaceable by a preloaded discharge spring, a dose setting element with at least two different rotational positions relative to the housing, and a dosing sleeve. The dosing sleeve or the plunger rod has a dose selection stop, and the other has at least one dosing stop. By rotating the dose setting element, the dosing sleeve or the plunger rod is rotated relative to the other. Upon displacement of the needle protection sleeve, the spring displaces the plunger rod, whereby, if the dose setting element is in the first rotational position, the dose selection stop and the first dosing stop strikes against each other, and, if the dose setting element is in the second rotational position, one of the dose selection stop and the first dosing stop is or can be moved past the other.

15 Claims, 24 Drawing Sheets

(51) Int. Cl.
    *A61M 5/31*    (2006.01)
    *A61M 5/32*    (2006.01)

(52) U.S. Cl.
    CPC ...... *A61M 5/3156* (2013.01); *A61M 5/31501*
        (2013.01); *A61M 5/31536* (2013.01); ***A61M
        5/3204* (2013.01); *A61M 5/3257*** (2013.01);
        *A61M 5/326* (2013.01); *A61M 2005/2013*
        (2013.01); *A61M 2205/581* (2013.01); *A61M
        2205/582* (2013.01)

(56) References Cited

FOREIGN PATENT DOCUMENTS

| | | |
|---|---|---|
| WO | 2006057604 A1 | 6/2006 |
| WO | 2010081489 A1 | 7/2010 |
| WO | 2011126439 A1 | 10/2011 |
| WO | 2013016832 A1 | 2/2013 |
| WO | 2013048310 A1 | 4/2013 |

OTHER PUBLICATIONS

International Search Report dated Oct. 8, 2015 for International Application No. PCT/CH2015/00104, 6 pages.

\* cited by examiner

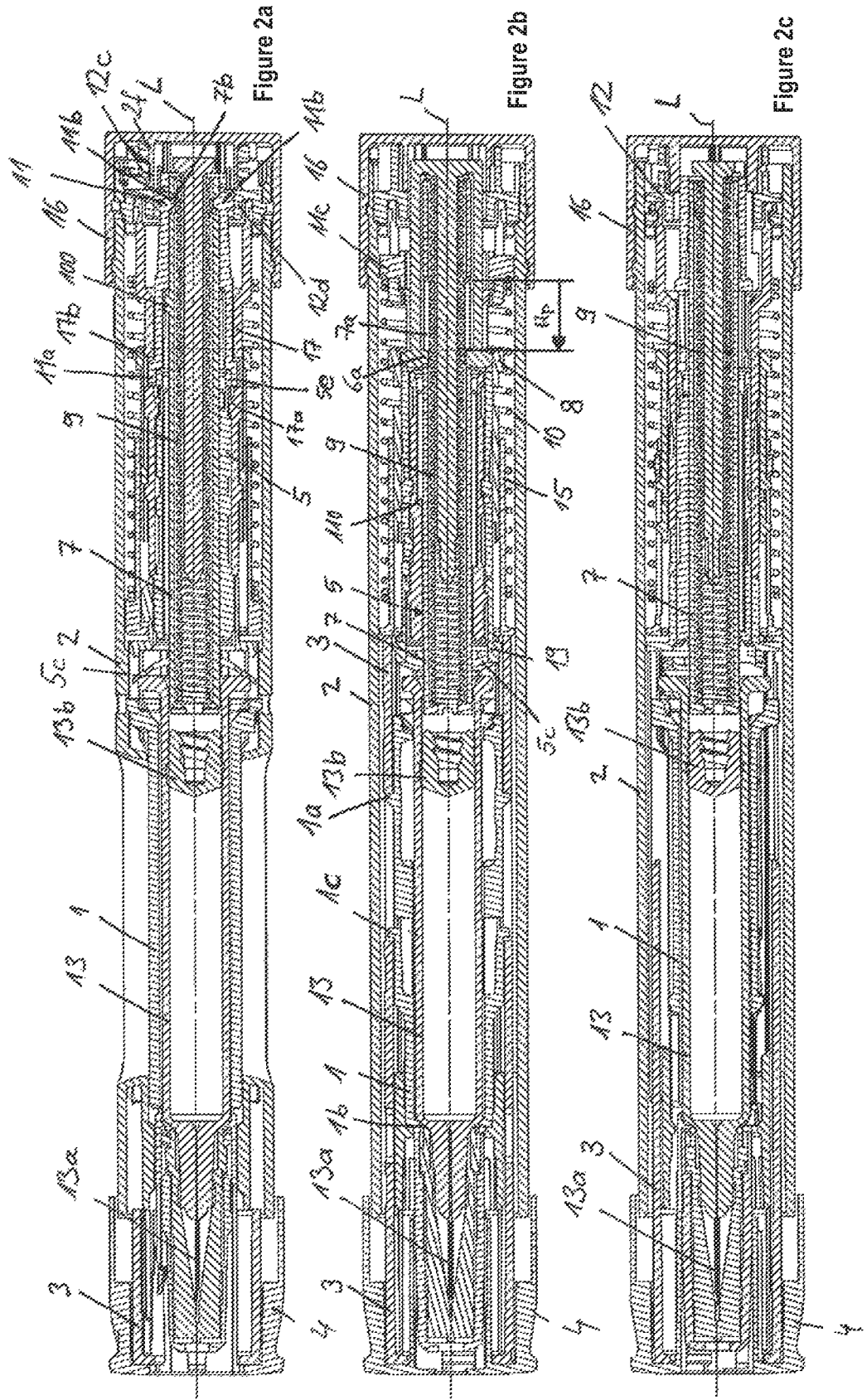

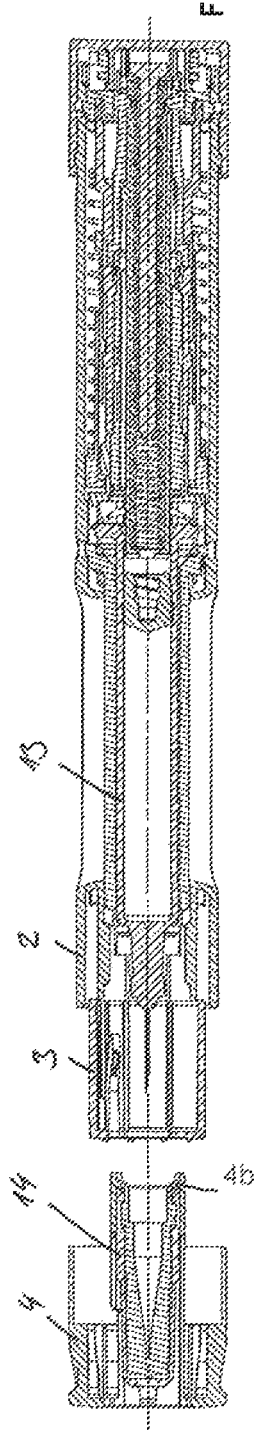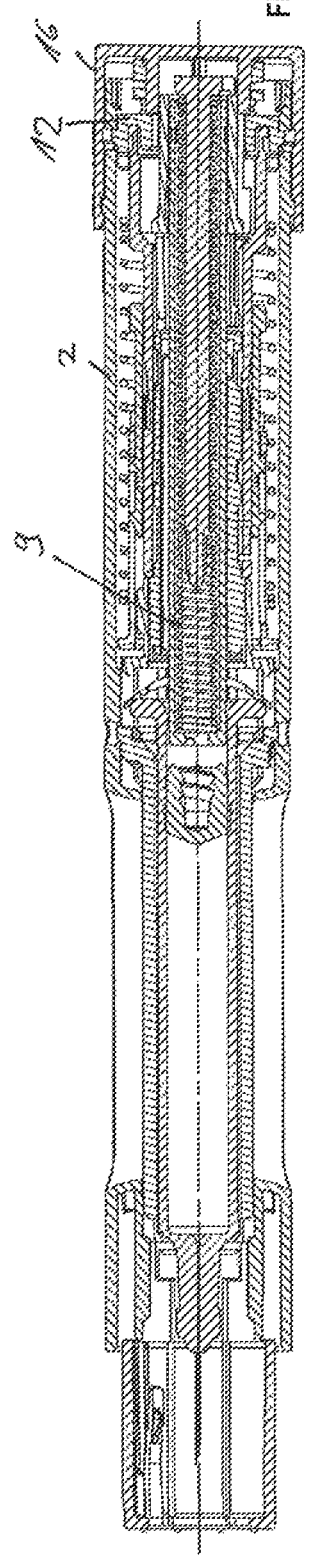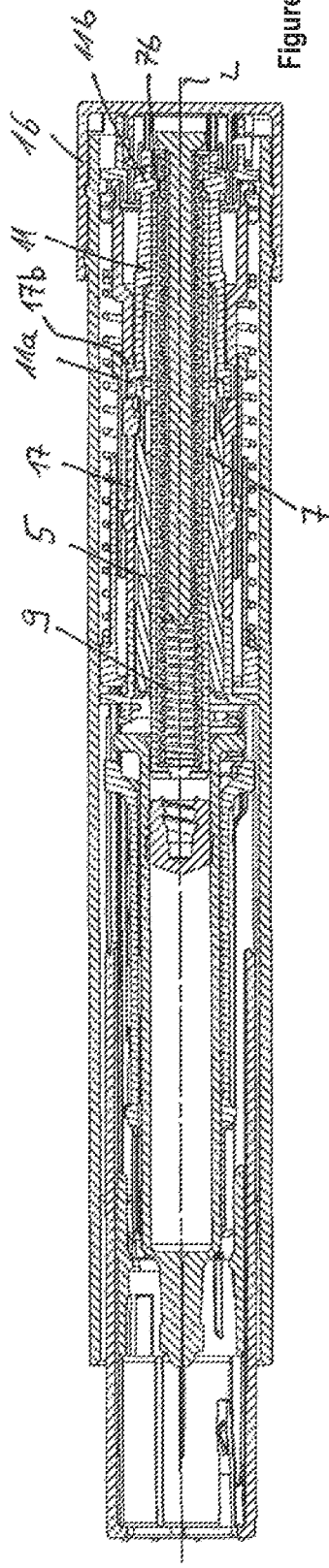

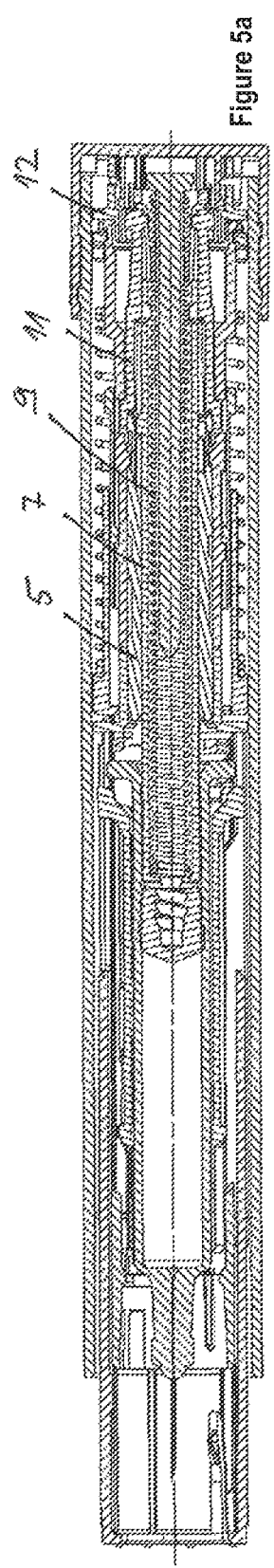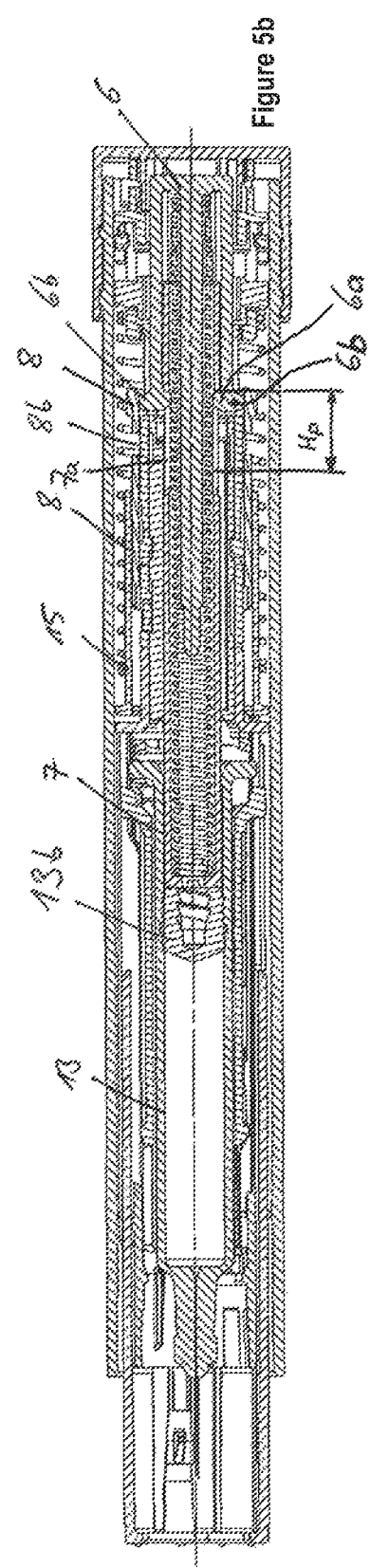

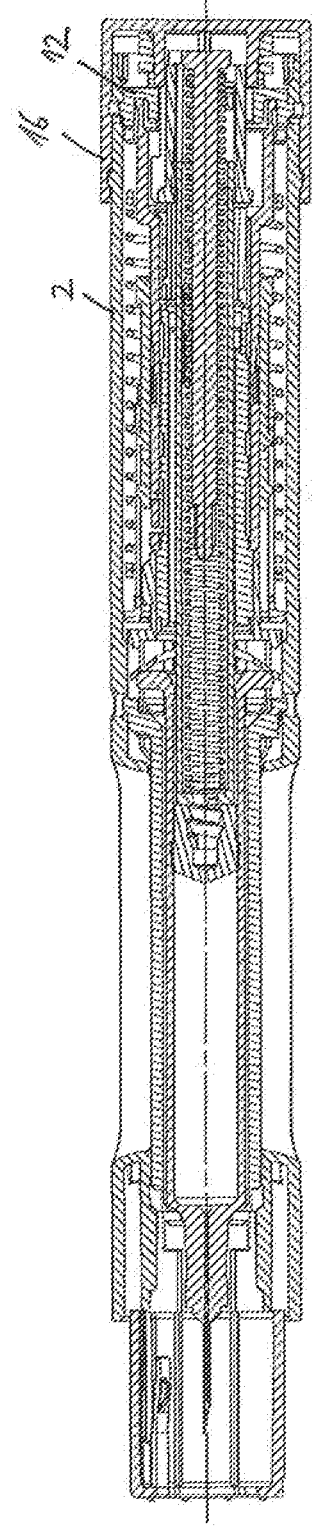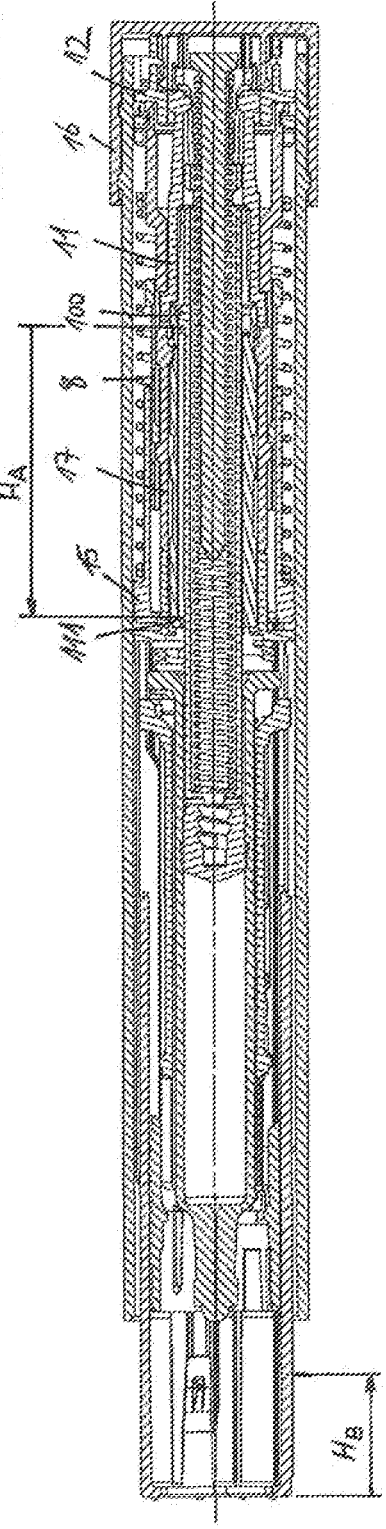

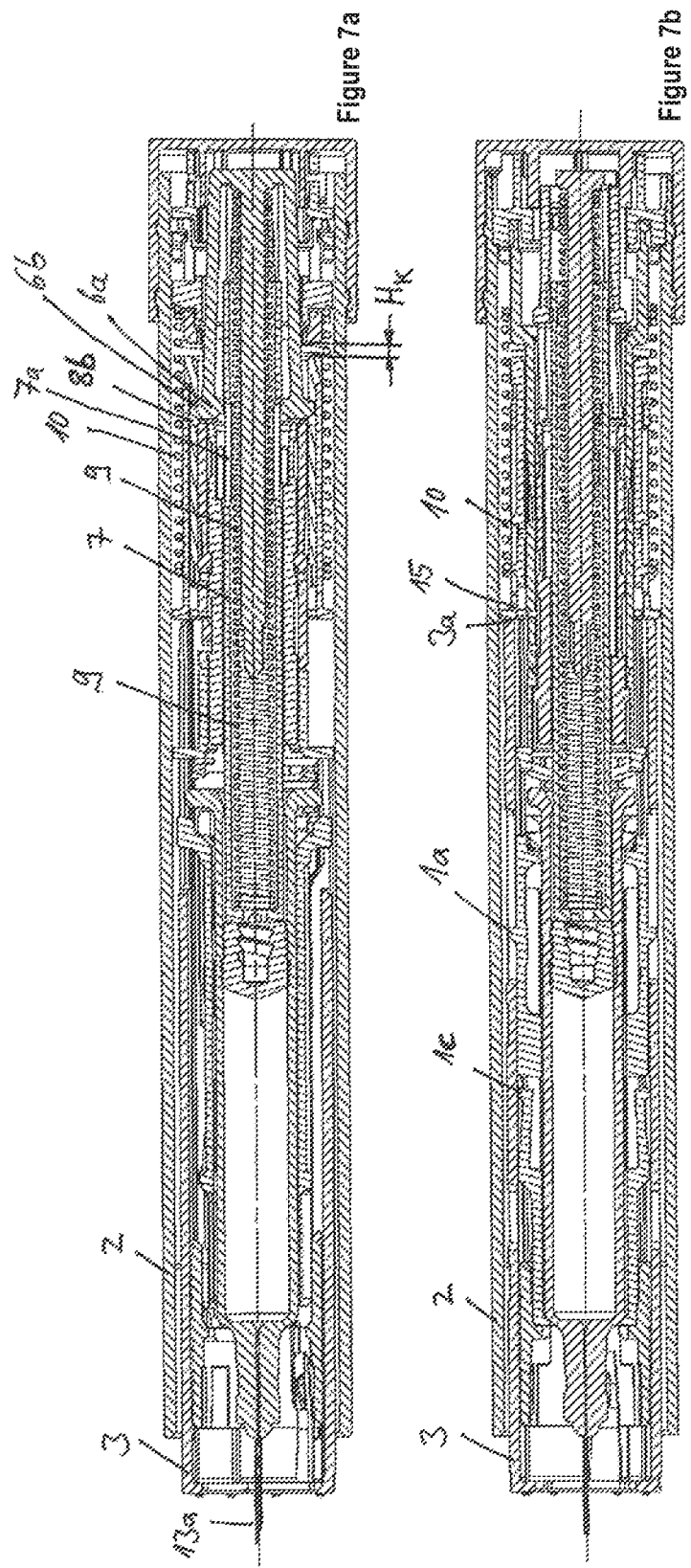

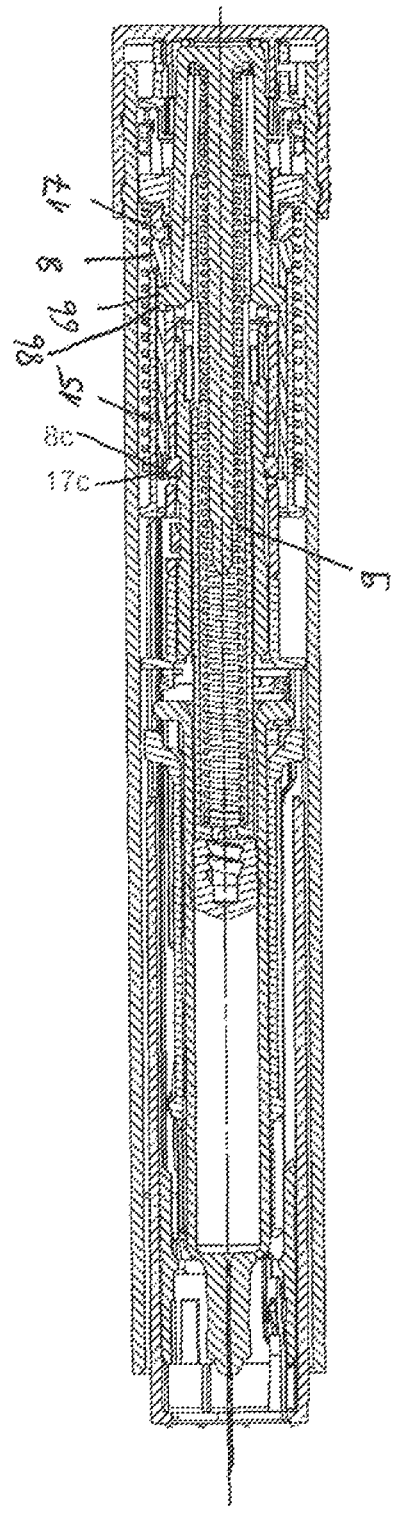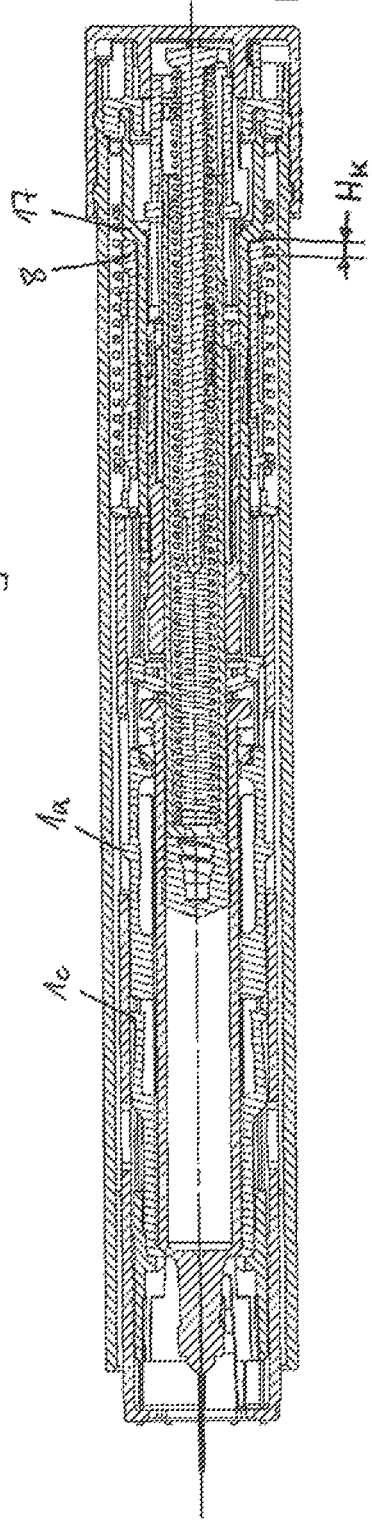

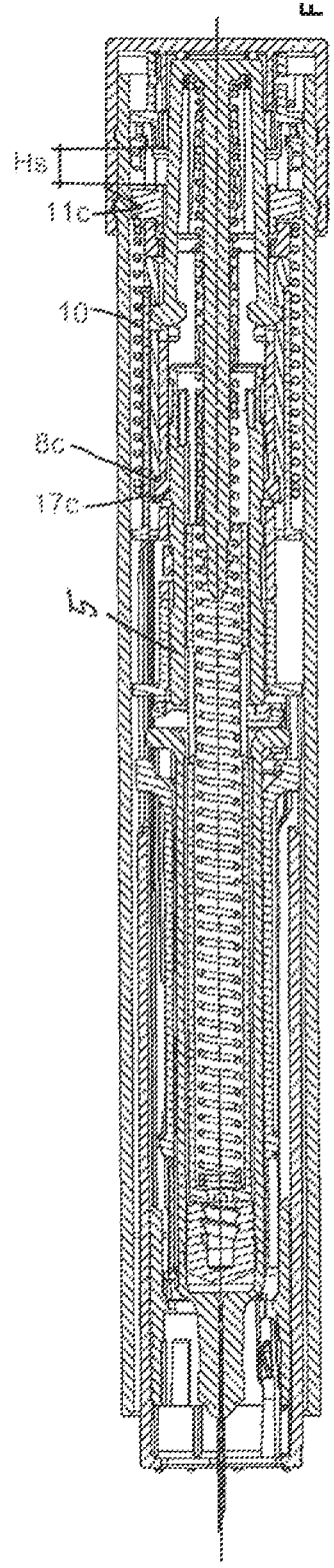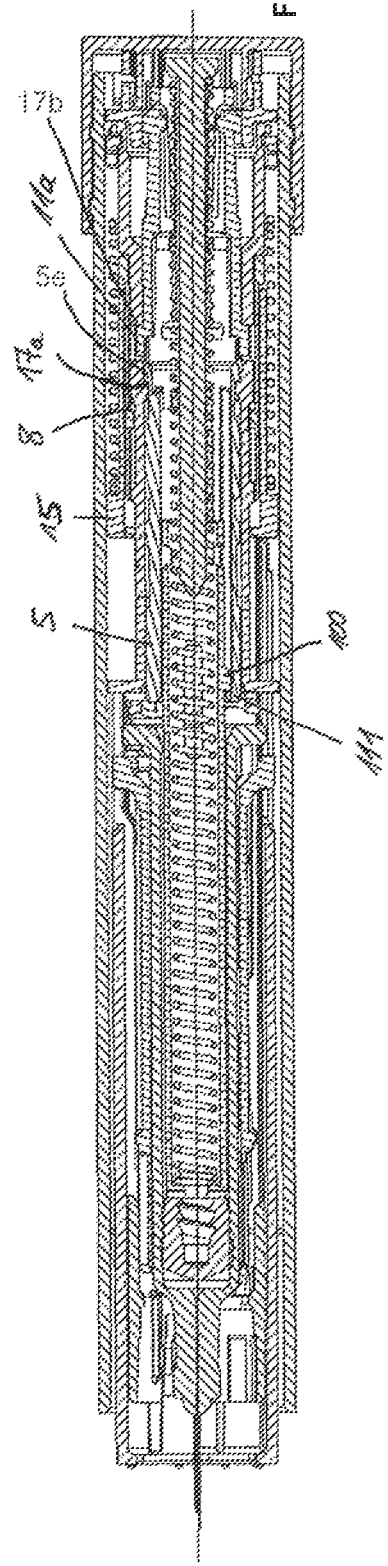

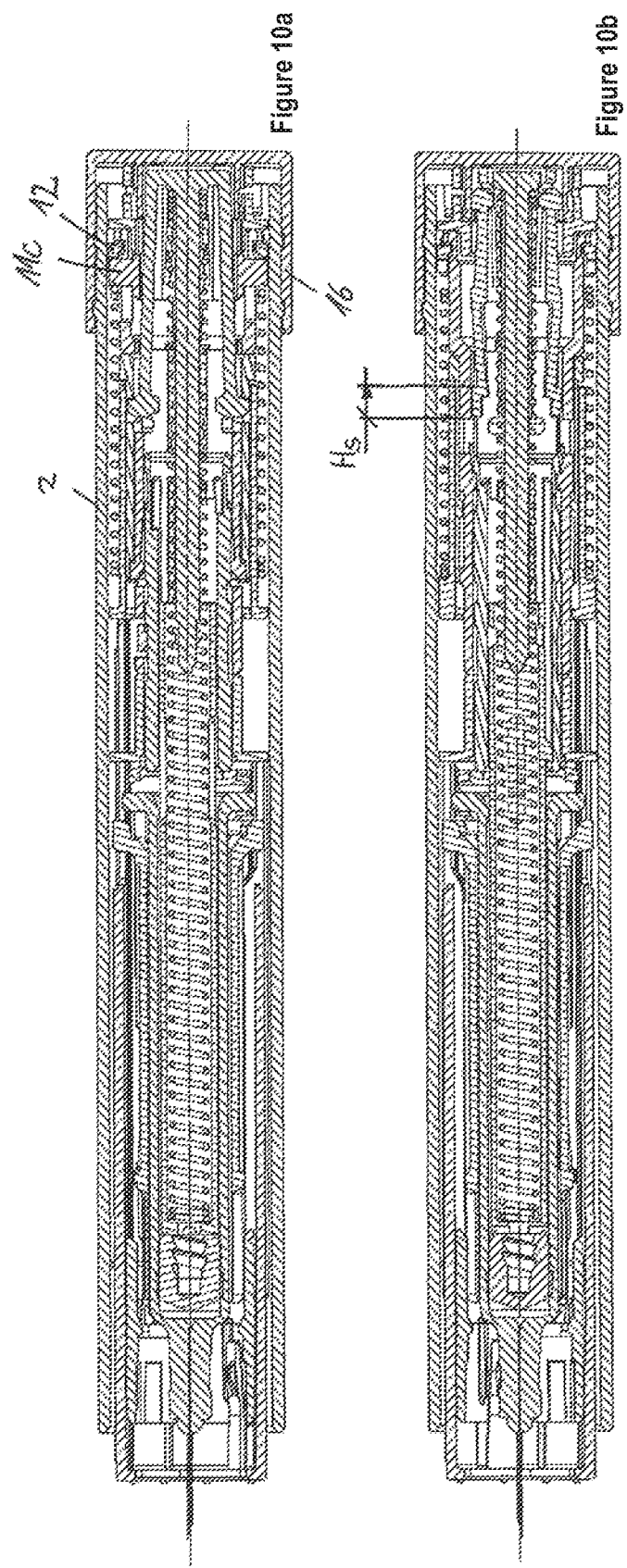

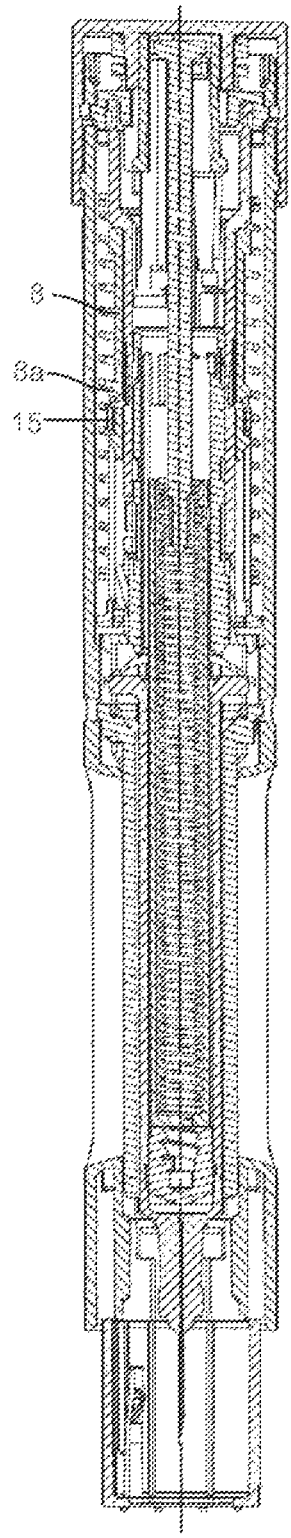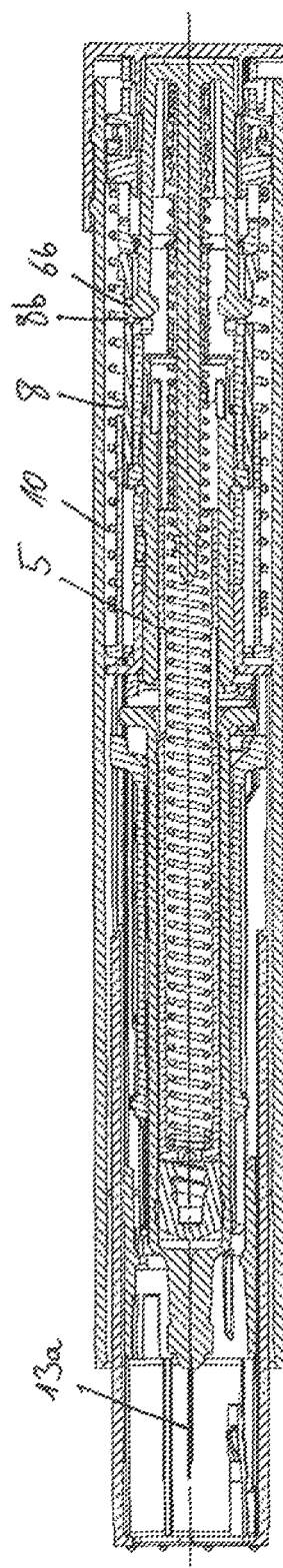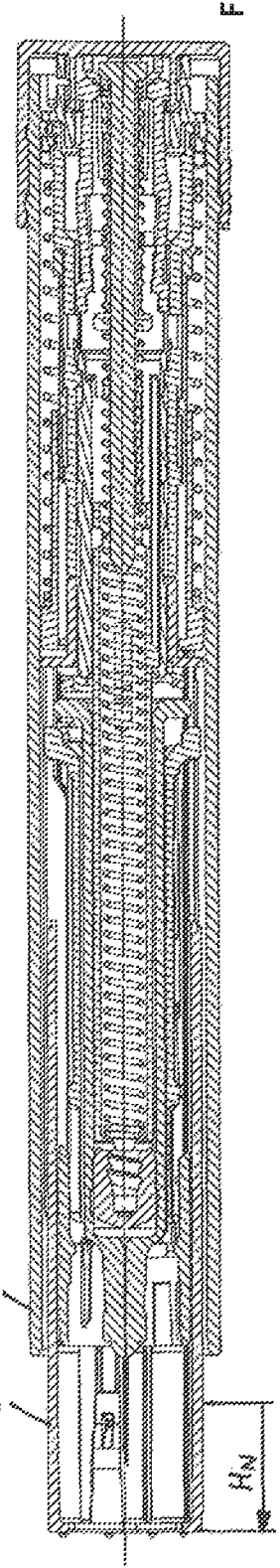

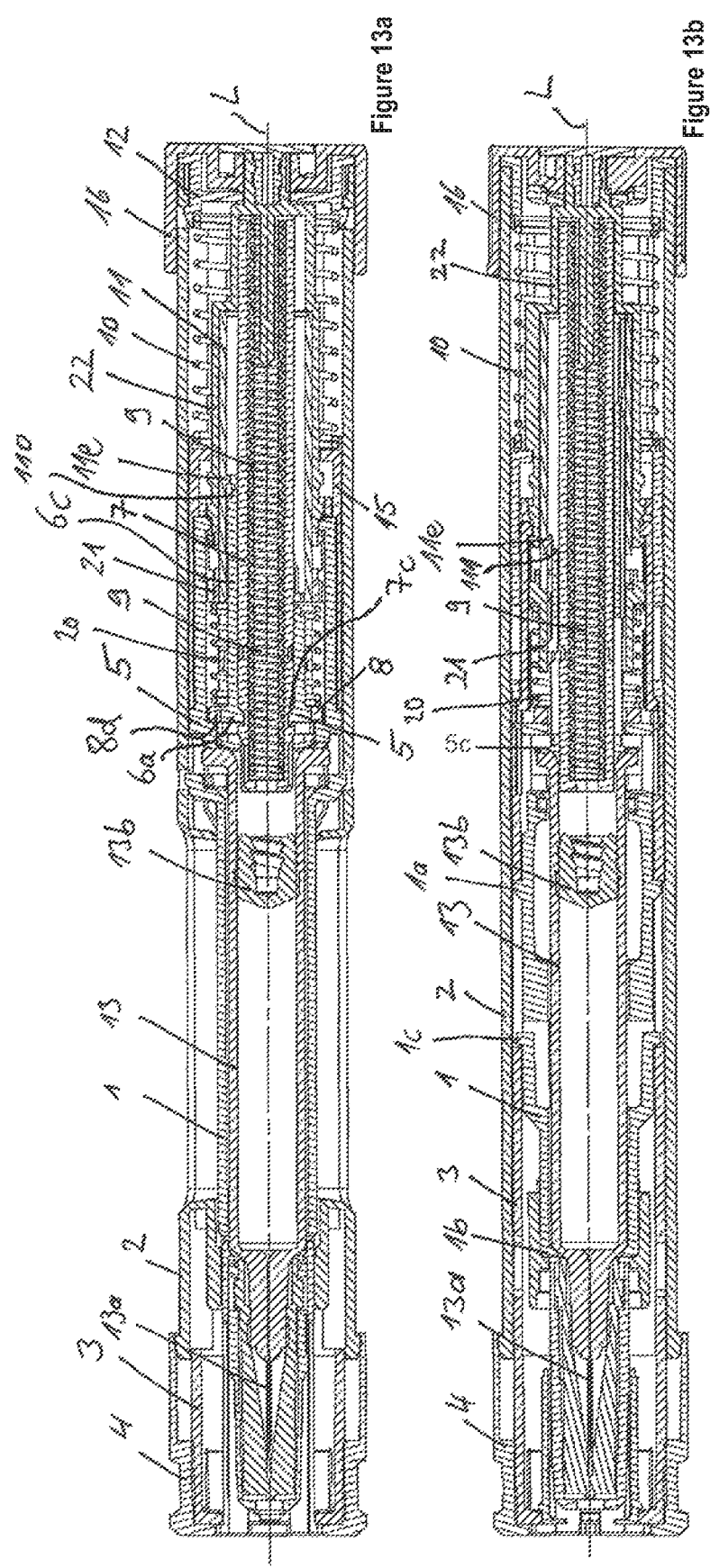

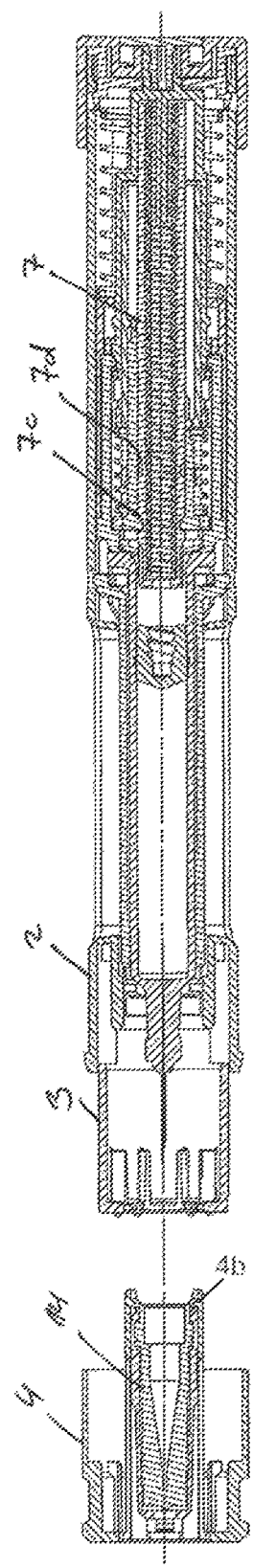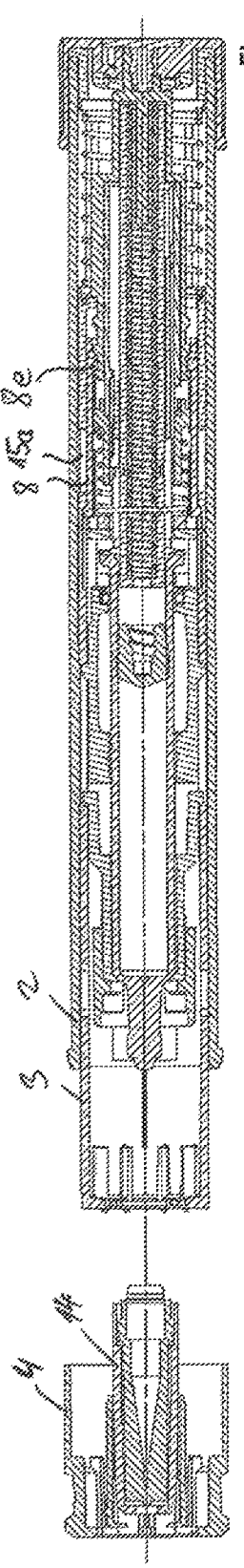

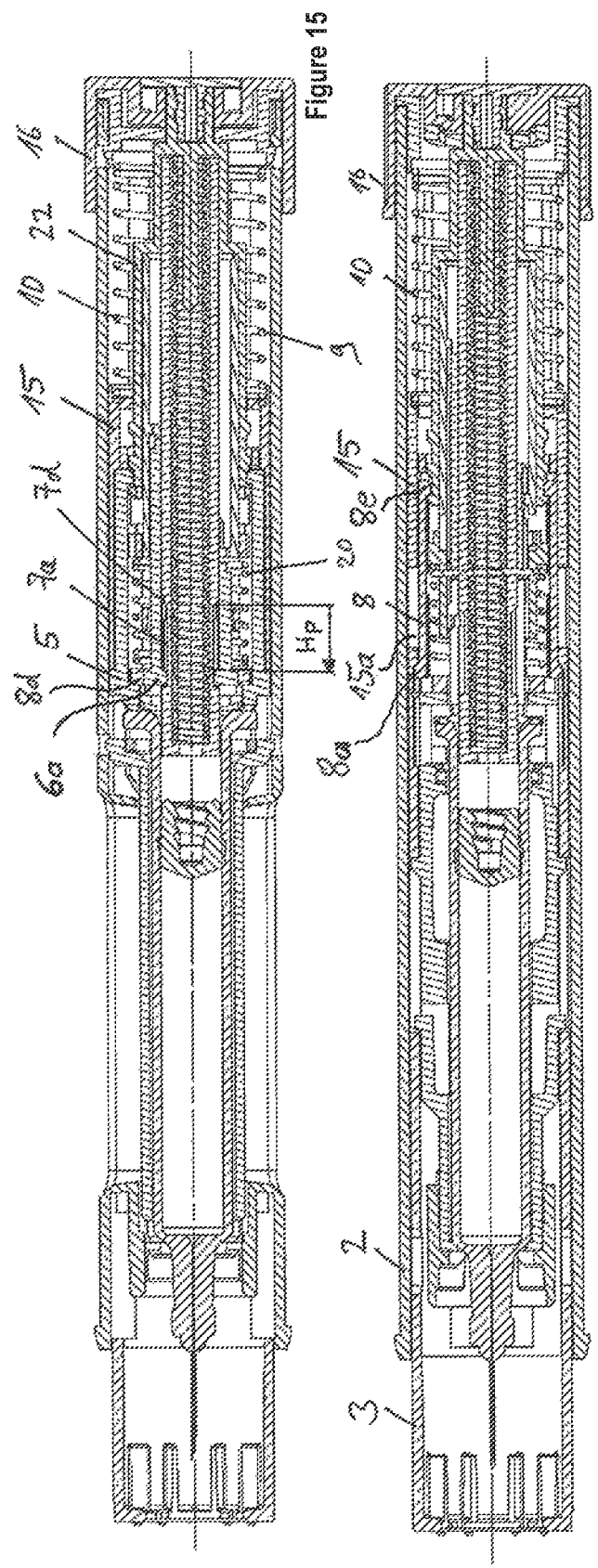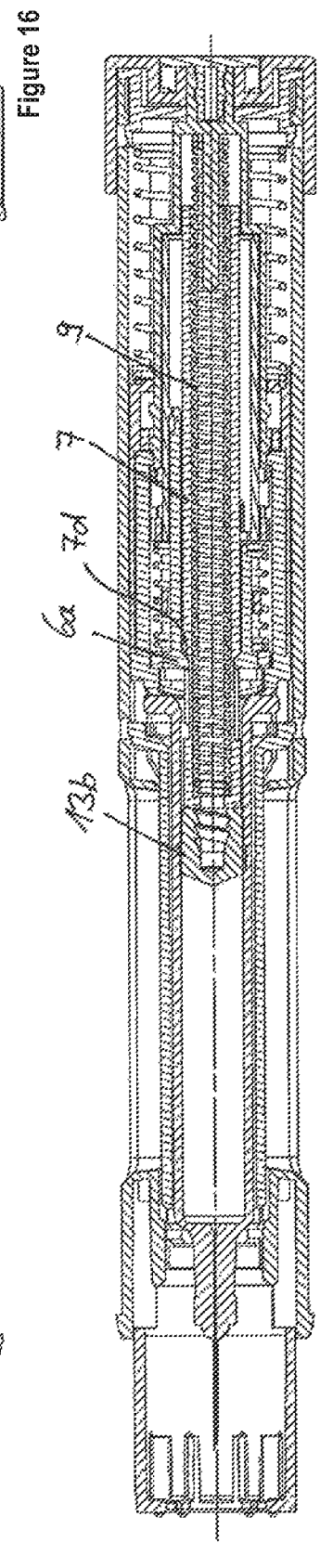

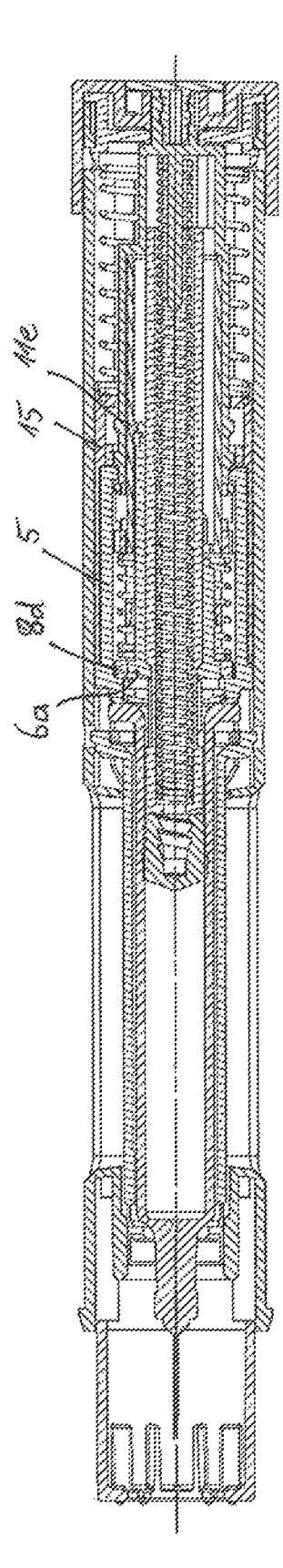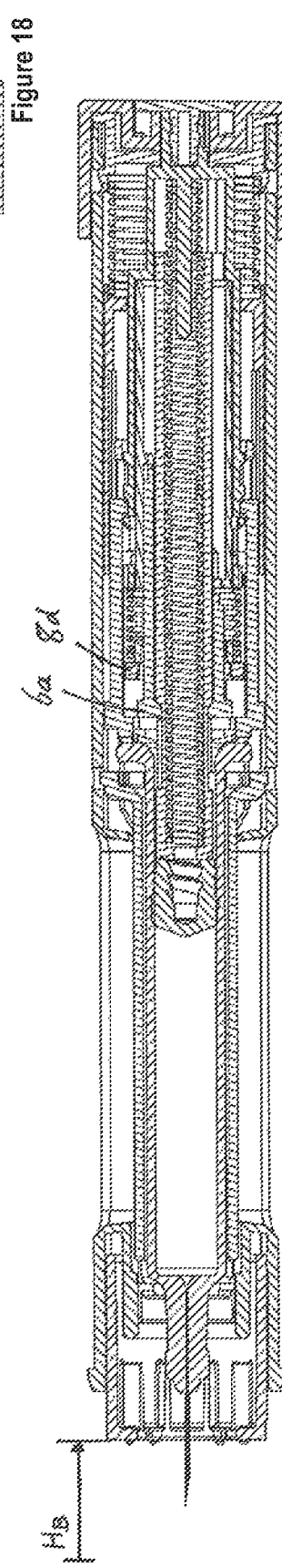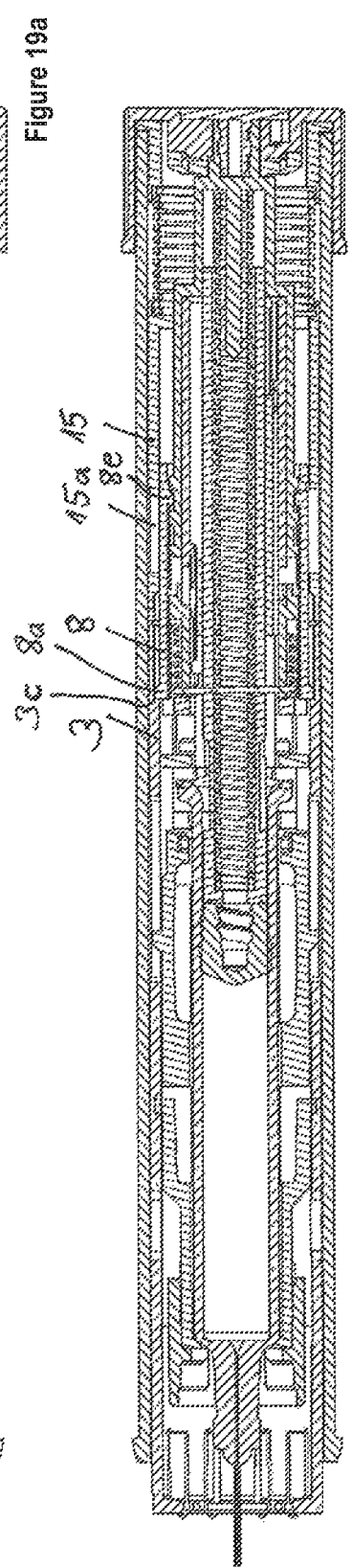

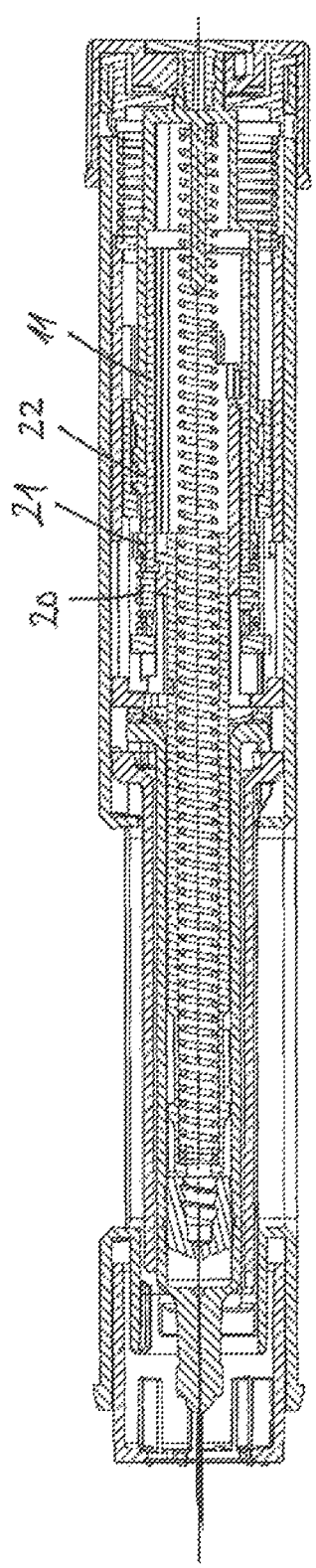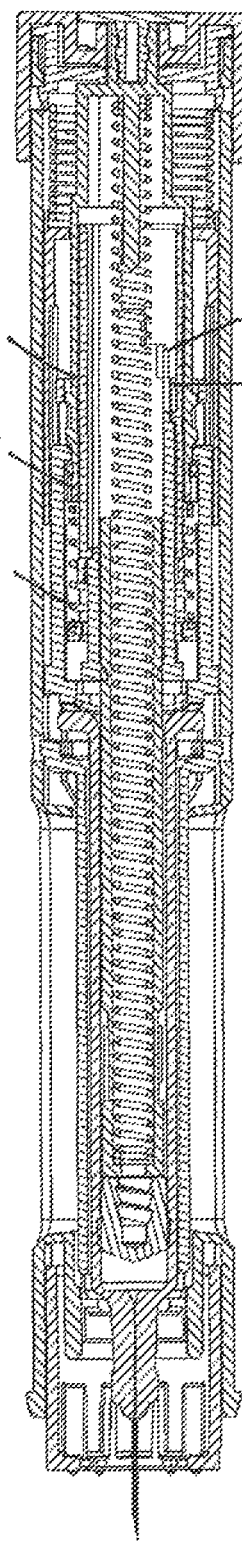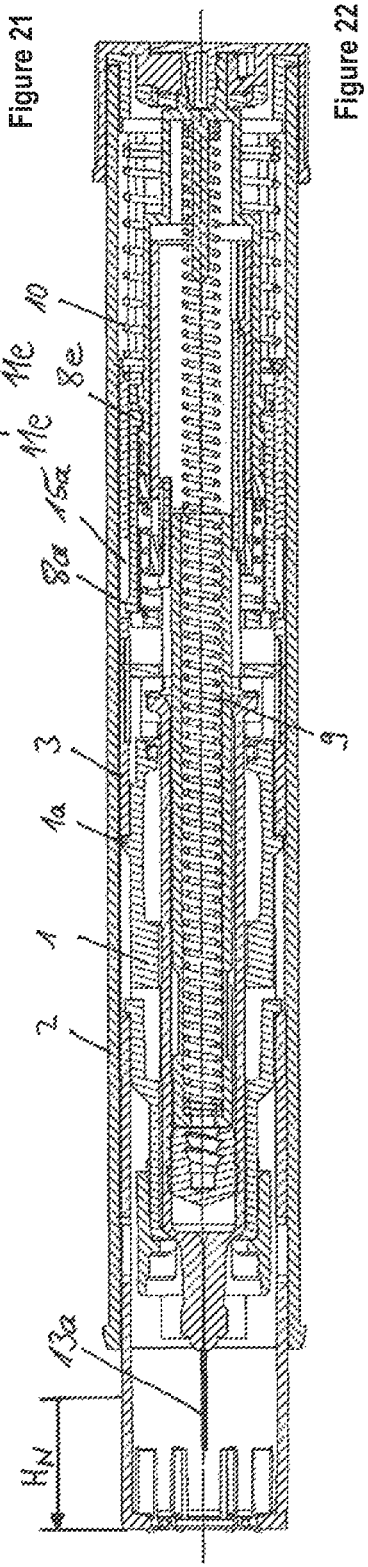

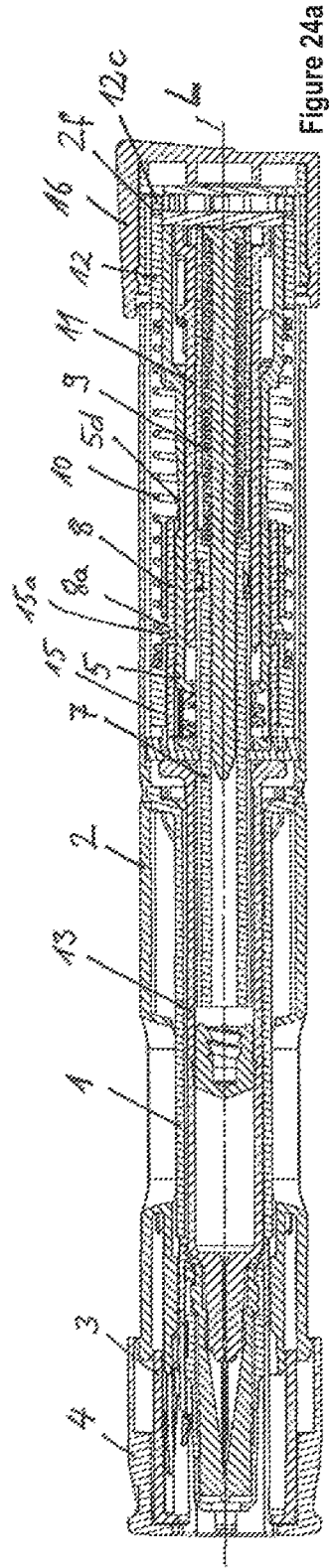

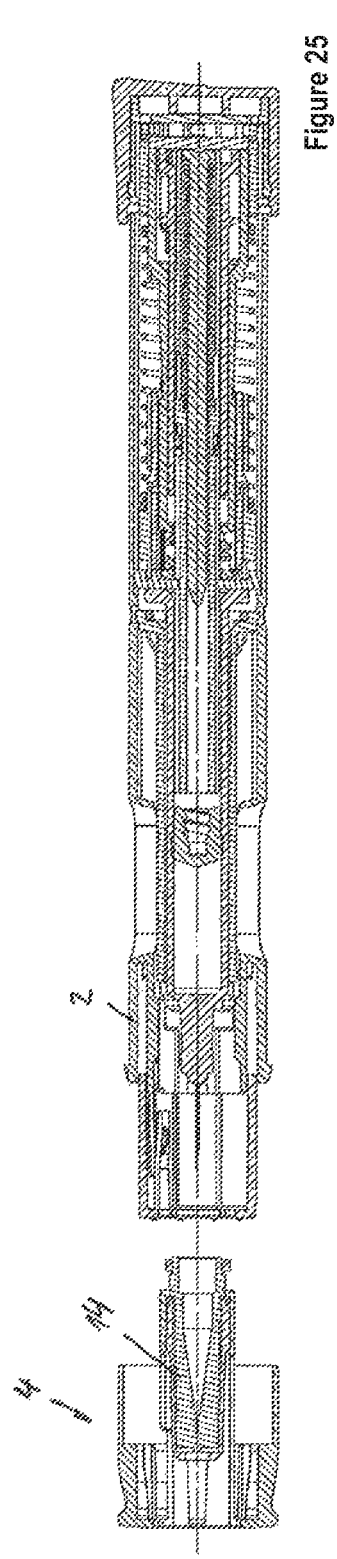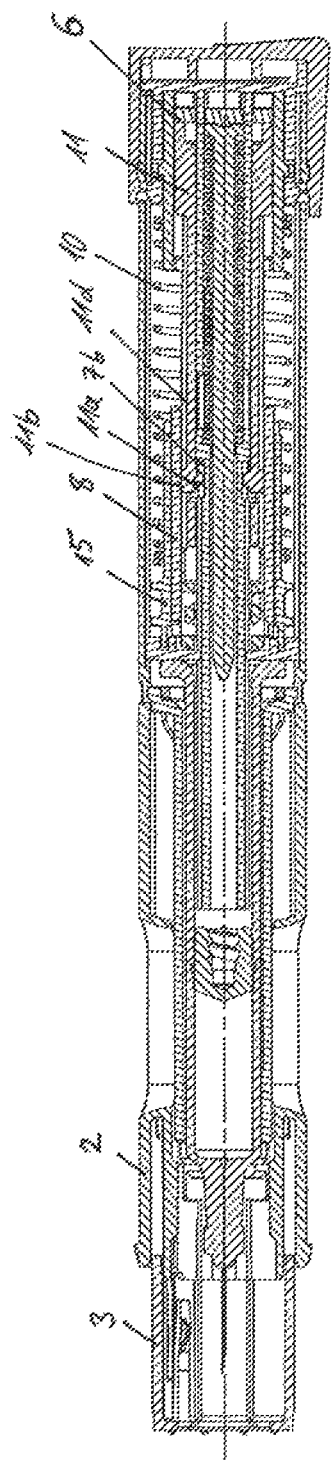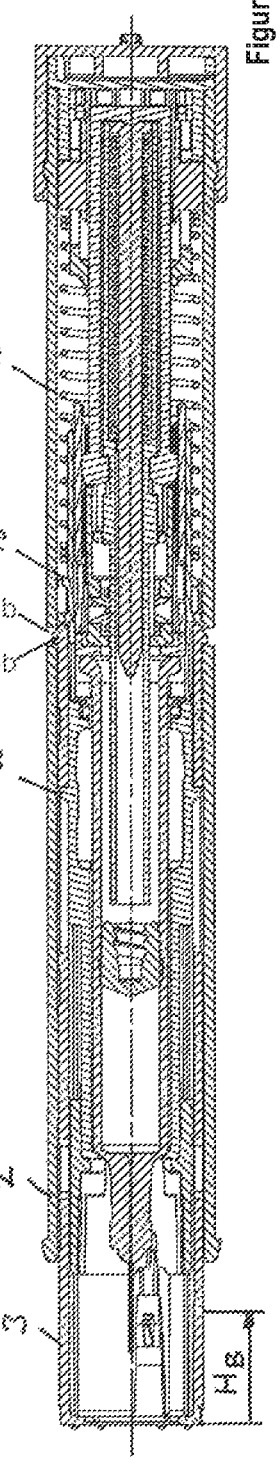

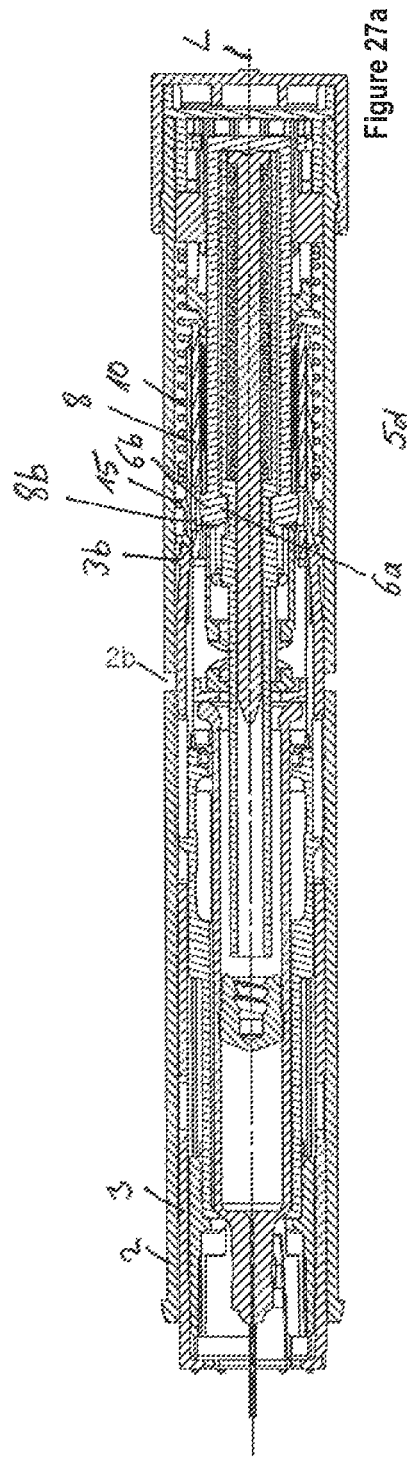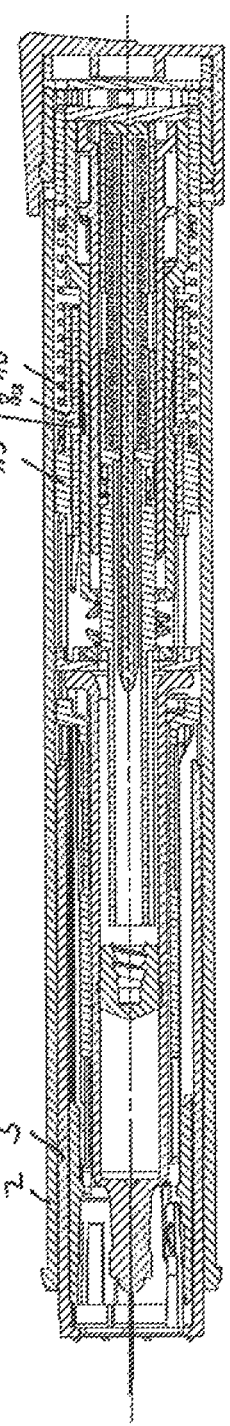
Figure 27a
Figure 27b

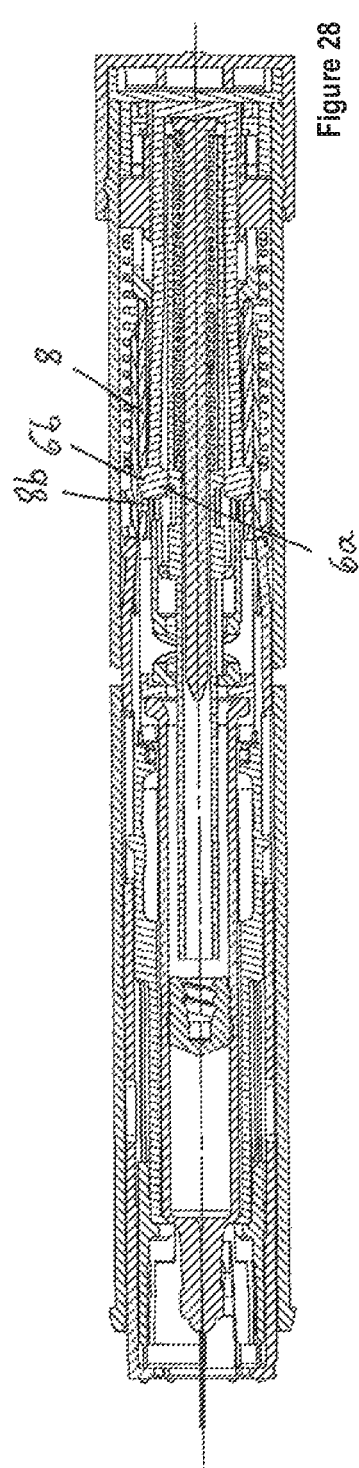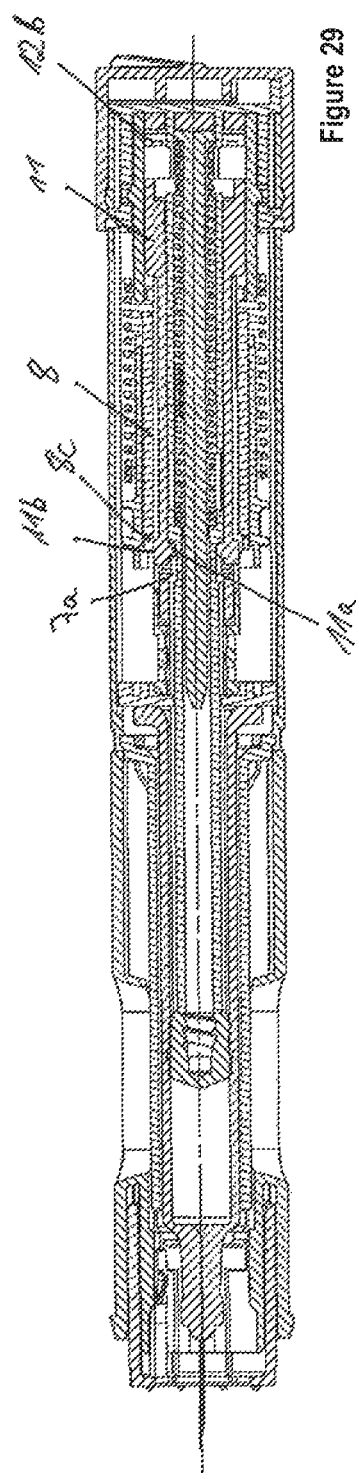

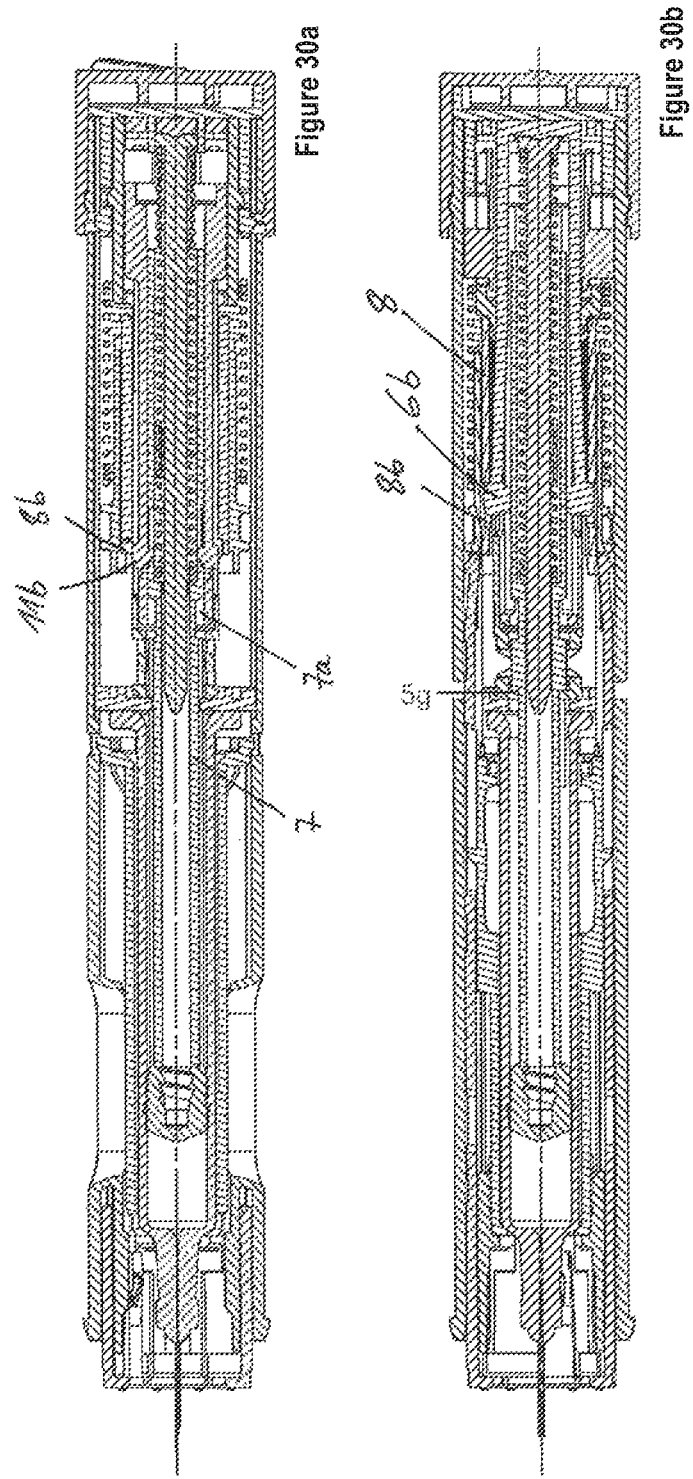

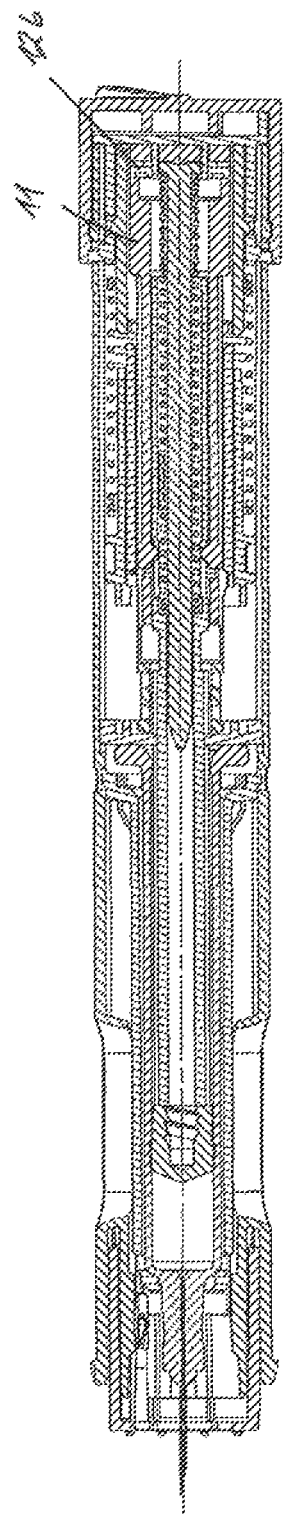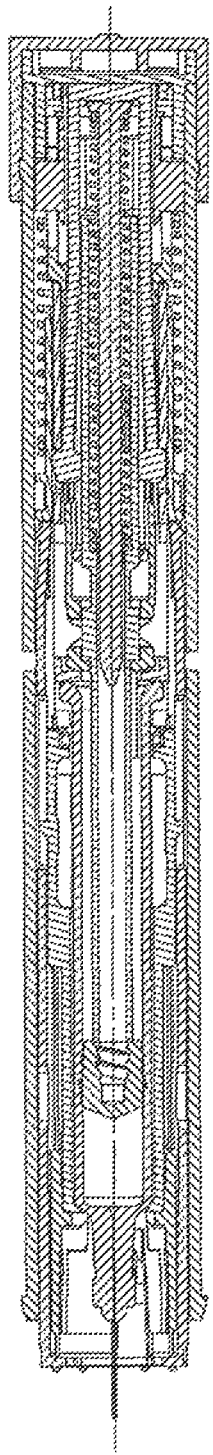
Figure 31a
Figure 31b

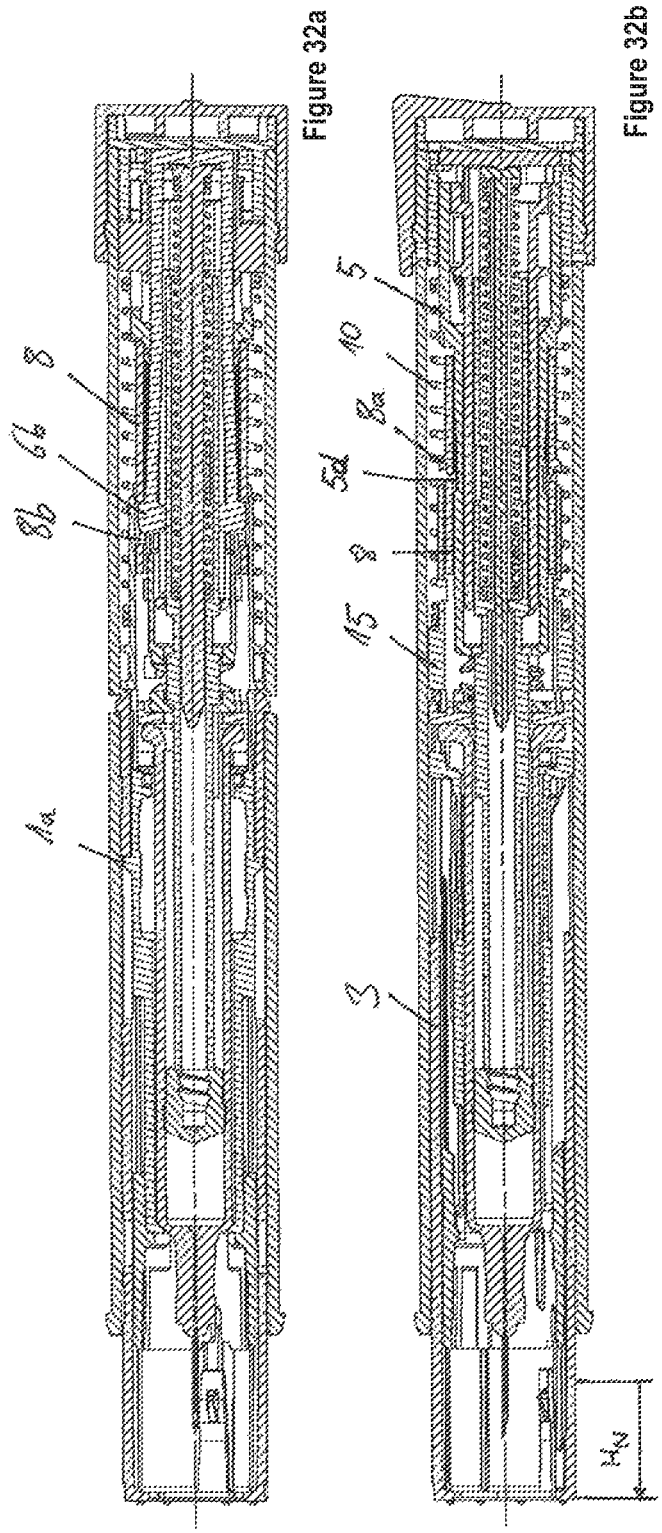

AUTOINJECTOR HAVING A SETTABLE DOSE

CROSS-REFERENCE TO RELATED APPLICATIONS

This application is a Continuation of International Patent Application No. PCT/CH2015/000104 filed Jul. 13, 2015, which claims priority to Swiss Patent Application No. CH 01161/14 filed Jul. 29, 2014. The entire contents of each are incorporated herein by reference for any and all purposes.

BACKGROUND

The invention relates to an autoinjector for administering a settable dose of a fluid product, in particular medication. The autoinjector is preferably designed so that using it, a dose setting and only a single product discharge are possible, and, after the single product discharge, the autoinjector is in a state that prevents an additional product discharge. A product quantity that has not been discharged remains in the autoinjector. Such autoinjectors can be referred to as a single-shot or single-use autoinjector device.

The term "medication" here comprises any free-flowing medicinal formulation that is suitable for controlled administration through a means such as, for example, a cannula or hollow needle, comprising, for example, a liquid, a solution, a gel or a fine suspension, which contains one or more medicinal active substances. A medication can be a composition with a single active ingredient or a premixed or co-formulated composition with several active ingredients from a single container. Medications include drugs such as peptides (for example, insulins, insulin-containing medications, GLP-1-containing as well as derived or analogous preparations), proteins and hormones, biologically obtained or biologically active ingredients, active ingredients based on hormones or genes, nutrient formulations, enzymes, and other substances either in solid (suspended) or fluid form, but also polysaccharides, vaccines, DNA or RNA or oligonucleotides, antibodies or parts of antibodies as well as suitable base, auxiliary and carrier substances.

Autoinjectors are known from the prior art. From EP 2 742 962 A2, an autoinjector according is designed so that it can only completely discharge the product quantity contained in its product container with a single injection.

For certain therapies, it can be necessary to discharge only a certain quantity of the product contained in the product container. One approach would be to fill the product container only with a desired product dose, so that the complete discharge of the product corresponds to the discharge of the desired product dose. However, in that case, for example, in a pharmacy, different autoinjectors with the same drug but different filling quantities of the product container thereof would have to be stored. It is simpler to provide an autoinjector that is filled with a larger product quantity as desired and that is suitable for discharging only some of this product quantity, wherein the autoinjector including the residual quantity of the product remaining in the autoinjector is disposed of.

SUMMARY

One problem of the invention is to provide an autoinjector that enables the setting of a product dose to be discharged.

The problem is solved with an autoinjector having the features and advantageous improvements from the claims, the description and the figures.

The invention provides an autoinjector for administering a fluid product, in particular medication, wherein the autoinjector comprises:

a. a housing, which is preferably sleeve-shaped and elongate with a longitudinal axis, b. a product container, in particular a syringe, at a distal end of which a needle is arranged, in particular detachably or non-detachably, in which a piston is displaceably arranged, which preferably forms a seal in contact with the wall of the product container surrounding it, and which is retained in a product container holder, which can also be referred to as syringe holder, wherein the product container holder is connected to the housing in an axially-fixed manner, preferably permanently, in particular by a snap connection or by a positive-lock connection, wherein the needle protrudes or projects from the housing beyond the distal end of the housing, c. a needle protection device, which, in particular, has the function of a needle protection sleeve and of a triggering device for the product discharge, wherein the needle protection sleeve can be displaced from an initial position, in which the distal end of the needle protection sleeve is distally beyond the needle tip of the needle, in such a manner that, in particular, access to the needle is prevented, into the housing, in particular in the proximal direction, so that the needle protrudes from the distal end of the needle protection sleeve, in particular over a length that corresponds approximately to the insertion depth of the needle, preferably for subcutaneous injection, and d. a plunger rod (e.g., tappet or transmission element) and a discharge spring, wherein it is preferable that the discharge spring is a coil spring acting as a compression spring, wherein the plunger rod is arranged in the housing and can be displaced by the preloaded discharge spring—in particular in the delivery state of the autoinjector—which is preferably arranged at least partially within the preferably sleeve-shaped plunger rod, along a longitudinal axis of the autoinjector or of the housing in the distal direction, wherein, as a result of the displacement of the plunger rod in the distal direction, the piston, against which the plunger rod strikes at least during the displacement, is entrained or slaved by the plunger rod and displaces the product from the product container, in particular via the needle.

The autoinjector moreover comprises a dose setting element, which preferably forms an outer surface of the autoinjector and which can be gripped by the user of the injector, wherein, in order to set a dose of the product to be discharged from the product container, the dose setting element can be turned in relation to the housing, in particular by the muscle force of the user, and assume at least two different rotational positions in relation to the housing, which preferably quasi-stable rotational positions are in particular specified by means of lock-in positions. A quasi-stable rotational position is understood to mean that the dose setting element can be turned relative to the housing only with increased torque from the respective quasi-stable rotational position, wherein the increased torque for loosening the quasi-stable rotational position is clearly higher than the sliding and/or adhesive friction for turning the dose setting element between the at least two specified rotational positions.

The autoinjector moreover comprises a dosing sleeve, wherein one of the dosing sleeve and the plunger rod has a dose selection abutment and the other of the dosing sleeve and the plunger rod has at least one dosing abutment, wherein, as a result of the turning of the dose setting element, one of the dosing sleeve and the plunger rod is turned in relation to the other of the dosing sleeve and the plunger rod. The part that is turned is connected or coupled, in particular directly or indirectly, i.e., via other parts of the autoinjector, to the dose setting element. For example, as a result of the turning of the dose setting element, a turning of the dosing sleeve relative to the plunger rod can occur. Alternatively, the turning of the dose setting element can cause a turning of the plunger rod relative to the dosing sleeve. The part that is not turned during the turning of the dose setting element can be connected in a rotationally fixed manner, directly or indirectly, i.e., via at least one other part, to the housing of the autoinjector.

In a first rotational position of the at least two rotational positions, the dose selection abutment and a first dosing abutment of the at least one dosing abutment are arranged in alignment along the longitudinal axis. In alignment is understood to mean, in particular, that the dose selection abutment and the corresponding dosing abutment face one another along the longitudinal axis and can strike one another with a purely translational movement along the longitudinal axis.

In a second rotational position of the at least two rotational positions, the dose selection abutment is angularly offset about the longitudinal axis relative to the first dosing abutment. i.e., in particular, for the angular offset, the longitudinal axis forms the rotation axis for the rotation angle. In principle, at least three, four or more rotational positions can be provided.

The displacement of the needle protection sleeve into the housing causes the discharge spring to displace the plunger rod in the distal direction, in particular it causes a release of an engagement blocking the plunger rod, which prevents the movement of the plunger rod in the distal direction, whereby, as a function of the rotational position of the dose setting element, product quantities of different sizes can be or are discharged. If the dose setting element is in the first rotational position thereof, one of the dose selection abutment and the first dosing abutment is moved toward the other—resting relative to the housing, for example—of the dose selection abutment and of the first dosing abutment. One of the dose selection abutment and the first dosing abutment thus strikes the other of the dose selection abutment and the first dosing abutment, in particular the one that is moving toward the other one.

When the dose setting element is in its second rotational position, one of the dose selection abutment and the first dosing abutment is or can be moved past the other of the dose selection abutment and the first dosing abutment along the longitudinal axis. As a result, the plunger rod can perform a larger stroke than when the dose setting element is in the first rotational position thereof, so that a larger dose can be discharged from the product container.

For example, the plunger rod can comprise the dose selection abutment and the dosing sleeve can comprise the at least one or a number of dosing abutments. Alternatively, the plunger rod can have the at least one dosing abutment or the multiple dosing abutments, wherein the dosing sleeve can have the dose selection abutment.

In an embodiment, the dose setting element can be a rotary knob attached on the proximal end of the housing, which can be gripped by the user of the autoinjector and turned by muscle force, wherein the dose setting element axially fixed relative to the housing can be turned, in particular connected by snap connection in an axially fixed manner and rotatably to the housing.

In addition, a lock-in device can be provided, which provides, in particular, the quasi-stable, lock-in positions for the dose setting element. In particular, the lock-in device can have, for example, for each lock-in position, a recess, a groove on the housing or on an element firmly attached to the housing, and a lock-in element which, depending on the rotational position of the dose setting element, engages in one of the recesses. The lock-in element can be attached on the dose setting element or a part connected in a rotationally fixed manner to the dose setting element, so that the lock-in element also turns with the dose setting element. Alternatively, for example, the lock-in device can have, for each lock-in position, a recess, in particular a groove on the dose setting element, and a lock-in element which, depending on the rotational position of the dose setting element, engages in one of the recesses. The lock-in element can be fastened on the housing or on an element firmly attached to the housing, so that the dose setting element turns relative to the lock-in element during the dose setting.

In addition, in the second rotational position of the at least two rotational positions, the dose selection abutment and a second dosing abutment of the at least one dosing abutment can be arranged in alignment along the longitudinal axis. One of the dose selection abutment and the second dosing abutment can move toward the other of the dose selection abutment and the second dosing abutment, wherein the other one is immobile, wherein, in particular, one of the dose selection abutment and the second dosing abutment strikes against the other of the dose selection abutment and the second dosing abutment, when the dosing setting element is in the second rotational position thereof, and the discharge spring displaces the plunger rod in the distal direction.

In addition, the first dosing abutment and the second dosing abutment can be at a distance from one another along the longitudinal axis and arranged with angular offset about the longitudinal axis. In particular, the angular offset between the first and second dosing abutments can correspond to the angular offset between the first and second rotational positions.

In addition, the product container can comprise an abutment which, in particular, can be formed by a tapering section between the cylindrical portion of the product container and the needle, against which the piston strikes, when the dose setting element is in the second rotational position thereof or in a third rotational position of the rotational positions thereof, and the discharge spring displaces the plunger rod in the distal direction. For example, when the dose setting element is in the third rotational position thereof, one of the dose selection abutment and the second dosing abutment is able to be moved or has been moved past the other of the dose selection abutment and the second dosing abutment along the longitudinal axis.

In general, the dosing sleeve or a part of the autoinjector that is different from the dosing sleeve and the product container can comprise an abutment, against which the dose selecting abutment of the plunger rod or another dose selection abutment of the plunger rod strikes, or is moved toward the dose selection abutment, when the dose setting element is in a second or in a third rotational position of the rotational positions thereof, and the discharge spring displaces the plunger rod in the distal direction. The part that is different from the dosing sleeve and from the product container can be connected or coupled, for example, in an axially-fixed manner to the housing, or it can be formed by the housing.

FIRST EMBODIMENT

In a first embodiment, the dose selection abutment can be formed on the plunger rod, wherein the at least one dosing abutment comprises a first dosing abutment and a second dosing abutment, which are formed on the dosing sleeve, wherein the dosing sleeve is rotationally fixed relative to the housing, and the plunger rod is connected in a rotationally fixed manner to the dose setting element and can be turned together with the dose setting element relative to the housing and/or the dosing sleeve.

In an addition to the first embodiment, the dosing sleeve can comprise a stop abutment, wherein a mechanism holder that is axially arranged relative to the housing and that preferably can be turned, which, in particular, can be snapped in an axially fixed manner and rotatably to the housing, can comprise a stop counter-abutment. The dose selection abutment, during the movement of the plunger rod in the distal direction, strikes against the first or second dosing abutment, depending on the rotational position of the dose setting element, and entrains the dosing sleeve in the distal direction, whereby the stop abutment is moved towards the stop counter-abutment, wherein the movement of the plunger rod and, in particular, of the dosing sleeve, in the distal direction is blocked, when the stop abutment strikes the stop counter-abutment.

Further, a displacement unit that comprises a first engagement unit that engages in a recess of the mechanism holder, so that the displacement unit is held in an axially fixed manner relative to the housing, wherein the first engagement unit is prevented by the dosing sleeve from moving out of the recess, when the stop abutment is at a distance from the stop counter-abutment, wherein, due to the entrainment of the dosing sleeve by the plunger rod, the dosing sleeve is or can be moved out of the position, in which the dosing sleeve prevents the first engagement unit from moving out of the recess. Advantageously, due to the discharge stroke, the entrainment of the dosing sleeve is achieved, and as a result the blocking of the first engagement unit is released.

An additional prestressed spring may additionally be provided, which can also be referred to as needle protection spring, which acts, in particular with the proximal end thereof, on the displacement unit and, for example, can act with a distal end thereof directly or preferably indirectly, such as, for example, via a switching sleeve, on the needle protection sleeve, whereby the displacement unit is moved or can be moved relative to the housing in the proximal direction, wherein, advantageously:

a. the displacement unit, during the movement in the proximal direction against an immobile part of the autoinjector, strikes and thereby generates a tactile and/or acoustic signal that signals the end of the discharge of the set dose, wherein the displacement unit is thus used as a signal generator or as a means for generating a signal, and/or b. the displacement unit, which is connected in a rotationally fixed manner to the mechanism holder and to the dose setting element, is moved or coupled by the movement in the proximal direction into a rotationally fixed and, in particular, positive-locking engagement with the housing or with an element that is firmly attached to the housing, so that the dose setting member is rotationally fixed relative to the housing about the longitudinal axis, wherein, for example, the displacement unit here acts as a coupling member, which is coupled in a rotationally fixed manner in the positive-locking engagement to the housing or to the element that is firmly attached to the housing. The displacement unit can move in the proximal direction, i.e., generate the signal and/or produce the relatively fixed coupling, only when the first engagement unit is moved or can be moved from the recess, i.e., when the dosing sleeve or the stop abutment thereof strikes the stop counter-abutment.

In addition to the first embodiment, the autoinjector that has been described in general, can also be provided with a second engagement unit, which is preferably formed by the displacement unit that detachably engages in a recess of the plunger rod, and as a result blocks the plunger rod in a movement relative to the housing in the distal direction, wherein, in an (initial) rotational position of the dose setting element, a retaining surface of the housing or of an element firmly connected to the housing prevents the second engagement unit from moving out of the recess, and, in the first and/or second rotational position or in a priming rotational position of the dose setting element, the retaining surface and the second engagement unit are separated with a rotational angle about the longitudinal axis, so that the second engagement element can be moved from the recess of the plunger rod, and the plunger rod can be moved for performing a priming stroke from the discharge spring in the distal direction. The priming stroke is used to displace any air contained in the product container from the product container and fill the fluid-conducting system up to the needle tip with the fluid product. As a result, it is prevented that air is injected into the patient, which is to be avoided.

In addition, the plunger rod can strike at the end of the priming stroke against a first engagement element engaging in a recess of the plunger rod, wherein it is preferable that the first engagement element be formed by a retaining element, against which the proximal end of the discharge spring is braced, wherein the first engagement element blocks a movement of the plunger rod in the distal direction in a detachable manner, wherein the needle protection sleeve, when it is moved into the housing, displaces a locking sleeve from a position, in which the locking sleeve prevents the first engagement element from being able to move from the recess of the plunger rod, in the proximal direction into a release position, wherein the locking sleeve has a recess, which, in the release position along the longitudinal axis, coincides approximately with the position of a second engagement element of the retaining element, wherein the second engagement element is preferably formed on the first engagement element, so that the second engagement element can be moved into the recess, and, at the same time, the first engagement element can be moved out of the engagement with the plunger rod, whereby the movement of the plunger rod in the distal direction is released for the discharge of the set dose.

SECOND EMBODIMENT

A second embodiment of the autoinjector is characterized in that the dose selection abutment is formed on the plunger rod, wherein the at least one dosing abutment comprises a first dosing abutment and a second dosing abutment, which are formed on the dosing sleeve, wherein the dosing sleeve engages in a rotationally fixed manner relative to the housing, in particular in a rotationally fixed manner in the housing or in a part that is firmly connected to the housing, wherein the plunger rod is connected or coupled in a rotationally fixed manner to the dose setting element and can be turned together with the dose setting element relative to the housing and/or the dosing sleeve. A turning of the dose setting element produces a rotation of the dose setting abutment relative to the first and second dosing abutments.

Naturally, more than two dosing abutments such as, for example, eight dosing abutments or more can be provided on the dosing sleeve.

For example, the dosing sleeve can be connected in an axially fixed manner to the housing, in particular by a snap connection. Alternatively, the dosing sleeve can be connected displaceably to the housing, wherein the dosing sleeve can be braced, for the axial fixation, against the proximal end of the syringe body of the product container.

In addition, the dosing sleeve can comprise, in particular, a flexible engagement element and/or an engagement element that can be moved toward the longitudinal axis, engagement element, which engages in a first recess of the plunger rod that, in particular, is formed in the shape of a slide, wherein the recess comprises a first abutment surface, which is in contact with the engagement element, whereby a movement of the plunger rod in the distal direction relative to the housing and/or the dosing sleeve is blocked. The first abutment surface can have been turned or be able to be turned by turning the dose setting element and, in particular, by the turning transferred thereby to the plunger rod, out of the contact with the engagement element, whereby the axial blocking of the plunger rod is released, and the plunger rod can be displaced by means of the drive spring by a priming stroke in the distal direction. At the end of the priming stroke, the engagement element is in contact with a second abutment surface that is preferably peripheral around the plunger rod in the form of a ring, and that is formed by the recess. The distance existing along the longitudinal axis between the first and second abutment surfaces corresponds substantially to the priming stroke. When the engagement element is in contact with the second abutment surface, the movement of the plunger rod in the distal direction is blocked.

In addition, the needle protection sleeve, when it is moved into the housing, in particular by means of a movement in the proximal direction and/or by an actuation stroke, can move a locking sleeve from a position, in which it prevents the engagement element from being able to move from the recess of the plunger rod, in the proximal direction into a release position, wherein the locking sleeve, in the release position, releases a movement of the engagement element out of the recess, in particular a movement of the engagement element transversely to the longitudinal axis, as a result of which the movement of the plunger rod in the distal direction is released for the discharge of the set dose, in particular the movement of the plunger rod for a discharge stroke.

In addition, the plunger rod can be coupled in a rotationally fixed manner to the dose setting element, when the engagement element is in contact with the first abutment and/or with the second abutment of the recess, and
   a. it is rotationally uncoupled from the dose setting element during the discharge of the dose, or
   b. rotationally uncoupled, when the dose selection abutment is in contact with the selected dosing abutment, in particular with a first or second dosing abutment. As a result, the dose setting element is rotationally uncoupled from the plunger rod, so that torque can no longer be transferred from the dose setting element to the plunger rod.

In addition, the autoinjector is characterized by a displacement unit, which is rotationally fixed and axially displaceable relative to the dosing sleeve, and which in particular surrounds the dosing sleeve and/or engages in a rotationally fixed manner or in an axially fixed displaceable manner in the dosing sleeve, and by a ring, which is rotatable about the longitudinal axis and which preferably surrounds the dosing sleeve and is mounted in particular on the dosing sleeve. The turnable ring is in an axially fixed engagement—which can be released by turning—with the dosing sleeve, at least in a direction along the longitudinal axis preferably in the proximal direction. The plunger rod, in particular the dose selecting abutment thereof, is designed so as to entrain the displacement unit toward the end of the discharge stroke, i.e., shortly before one of the dosing abutments or the selected dosing abutment is reached. In particular, during the discharge stroke, the dose selection abutment can strike against the displacement unit and entrain it, until the dose selection abutment strikes against one of the dosing abutments or the selected dosing abutment. The displacement unit comprises, for example, a beveled transmission surface which, for example, slides on a beveled gear counter-surface of the ring or in general on the ring, whereby the ring is turned about the longitudinal axis and out of the axially fixed engagement in which the ring stands with the dosing sleeve, so that a prestressed spring, in particular a coupling spring or snap spring, displaces or can displace the ring in the proximal direction.

In particular, the spring can accelerate the ring against an axially fixed part of the autoinjector, in particular a coupling sleeve, whereby, at the time of the striking against the axially fixed part, an acoustic and/or tactile signal is generated, which signals the end of the discharge of the selected dose. Alternatively or additionally, the spring can displace the ring in a rotationally fixed engagement, in particular in a groove of the dosing sleeve extending along the longitudinal axis, whereby the ring is coupled in a rotationally fixed manner to the dosing sleeve and/or the housing. Furthermore, the displacement of the ring by the spring has the effect that the ring assumes a position, in which the ring engages in a rotationally fixed manner in the coupling sleeve, which in turn is coupled in a rotationally fixed manner to the dose setting element, so that, in particular, the turning of the dose setting element relative to the housing is blocked. For example, the ring, together with the coupling sleeve, can form a claw coupling, which can be coupled with the movement of the ring in the proximal direction into the rotationally fixed coupling engagement.

The coupling sleeve is preferably in a coupling engagement—which is, in particular, detachable—with a plunger rod, when the engagement element of the dosing sleeve is in contact with the first abutment and/or second abutment of the recess of the plunger rod, wherein the coupling engagement is being detached or is detached during the discharge of the dose, when the dose selection abutment is in contact with the selected dosing abutment.

THIRD EMBODIMENT

A third embodiment of the autoinjector is characterized in that the dose selection abutment is formed on the dosing sleeve, wherein the at least one dosing abutment comprises, for example, a first dosing abutment and, optionally, a second dosing abutment, wherein the dosing abutment or the dosing abutments are formed on a plunger rod, wherein the plunger rod is rotationally fixed relative to the housing, wherein the dosing sleeve is connected or coupled in a rotationally fixed manner to the dose setting element and can be turned together with the dose setting element relative to the housing and/or the plunger rod, wherein the dosing sleeve is connected, for example, in an axially fixed manner to the housing.

The dosing sleeve can comprise a main section, a spring section and a section resiliently arranged distally from the main section along the longitudinal axis by means of the spring section. The main section or the resiliently arranged section can form the dose selection abutment.

In addition, a rotation prevention sleeve, which connects the plunger rod and the housing in a manner that prevents rotation can be provided, wherein the rotation prevention sleeve is arranged between the resiliently arranged section of the dosing sleeve and a proximal end of the product container, in particular, a finger flange, so that the spring section of the dosing sleeve presses the product container via the rotation prevention section, which is preferably axially displaceable relative to the housing, into a firm seating with the product container holder.

BRIEF DESCRIPTION OF THE DRAWINGS

FIGS. 2a-2c show the first embodiment in a delivery state, wherein FIGS. 2a to 2c are cross-sectional views extending through the longitudinal axis of the device, wherein the longitudinal sections are angularly offset about the longitudinal axis.

FIG. 3 shows the first embodiment with a removed pull-off cap.

FIGS. 4a-4b show the first embodiment, wherein a priming is released.

FIGS. 5a-5b show the first embodiment after the priming.

FIGS. 6a-6b show the first embodiment during a dose setting.

FIGS. 7a-7b show the first embodiment in a state in which the needle protrudes over the distal end of the autoinjector and the autoinjector is released.

FIGS. 8a-8b show the first embodiment during the generation of a clicking sound, which signals the beginning of the injection.

FIGS. 9a-9b show the first embodiment in a state in which the product is discharged, FIGS. 10a-10b show the first embodiment during the generation of a clicking sound, which signals the end of the injection.

FIG. 11a-11c show the first embodiment in a state in which the needle protection sleeve covers the needle and is blocked from being pushed back.

FIG. 13a-13b show the second embodiment in a delivery state, wherein FIGS. 13a and 13b are cross-sectional views extending through the longitudinal axis of the device, wherein the cross-sectional views are angularly offset about the longitudinal axis.

FIGS. 14a-14b show the second embodiment with a removed pull-off cap.

FIG. 15 shows the second embodiment in a state, in which a priming is released.

FIG. 16 shows the second embodiment, wherein an insertion of the needle is released.

FIG. 17 shows the second embodiment in a state, in which the priming is carried out.

FIG. 18 shows the second embodiment in a state in which a dose selection has been carried out.

FIGS. 19a-19b show the second embodiment in a state in which a needle protrudes beyond the distal end of the autoinjector and releases an injection.

FIG. 20 shows the second embodiment, in which a clicking sound is issued, which signals the end of the injection.

FIG. 21 shows the second embodiment in a state in which the clicking sound, signaling the end of the injection, has been generated.

FIG. 22 shows the second embodiment with a needle protection sleeve locked against being pushed back, in a needle protection position.

FIGS. 24a-24c show the third embodiment in a delivery state, wherein FIGS. 24a to 24c are cross-sectional views extending through the longitudinal axis of the device, wherein the cross-sectional views are angularly offset about the longitudinal axis.

FIG. 25 shows the third embodiment with a removed pull-off cap.

FIGS. 26a-26b show the third embodiment during a dose setting.

FIGS. 27a-27b show the third embodiment in a released state.

FIG. 28 shows the third embodiment, wherein a signal signaling the start of the product discharge is generated.

FIG. 29 shows the third embodiment, wherein the generation of a signal signaling the end of the product discharge is prepared.

FIGS. 30a-30b show the third embodiment after the discharge of the product dose has occurred.

FIGS. 31a-31b show the third embodiment, wherein the signal signaling the end of the product discharged is generated.

FIGS. 32a-32b show the third embodiment with a needle protection sleeve blocked against being pushed back, in a needle protection position.

DETAILED DESCRIPTION

First Embodiment

Figure 1:
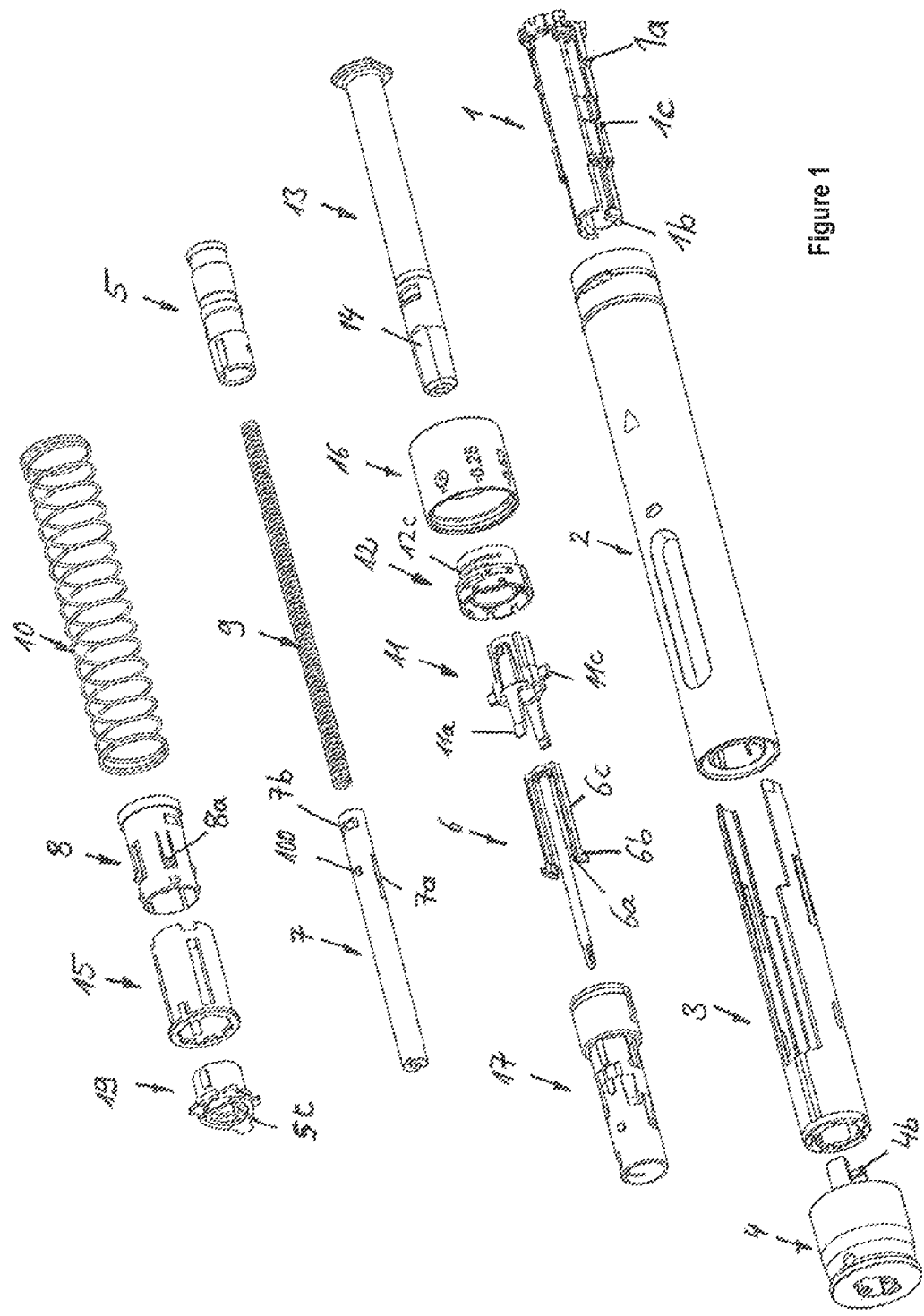
FIG. 1 shows an exploded view of an autoinjector according to a first embodiment.

In reference to FIGS. 1 to 11b, the structural features and the function of the autoinjector according to the first embodiment are now described.

The autoinjector comprises a sleeve-shaped, elongate housing 2 with a longitudinal axis L, which, at its proximal end, comprises a sleeve-shaped housing insert 12 that is connected with positive connection to the housing 2 in a rotationally and axially fixed manner, and that is arranged at the proximal end of the housing 2. The sleeve-shaped housing insert 12 comprises a lock-in catch 12c. A dose setting element 16 comprises several, in particular at least two, or in accordance with the number of settable doses, lock-in grooves 2f distributed over the periphery, wherein the lock-in catch 12c engages in the lock-in grooves 2f, and, when the dose setting element 16 is turned, for example, for a dose setting, the lock-in catch 12c is moved from the lock-in groove 2f and into another of the lock-in grooves 2f. As a result, quasi-stable lock-in positions for the dose setting element 16 are specified.

The sleeve-shaped dose setting element 16 is connected on the proximal end of the housing 2 rotatably and in an axially fixed manner to the housing 2, in particular by snap connection, and, in particular, it forms the proximal end of the autoinjector. The dose setting element 16 can be gripped by the user of the device and turned relative to the housing 2 by the muscle force of the user for the setting of a product dose to be discharged. For example, by means of the device, several variable doses can be set in different small increments. For example, the dose setting element 16 can assume, relative to the housing, at least two different quasi-stable rotational positions, or in accordance with the number of settable doses, for example eight different quasi-stable rotational positions, distributed over the periphery, wherein, in a first rotational position, a first dose is set, and, in a second rotational position, a second dose is set, etc.

On the distal end of the autoinjector, in its delivery state (FIGS. 2a to 2c), a pull-off cap 4 is arranged, which is pulled or twisted off, before the use of the autoinjector, and removed.

In the housing 2, a product container 13, in the form of a syringe, is accommodated in a manner so it cannot be displaced relative to the housing 2—except for the installation of the autoinjector—along the longitudinal axis L. The product container 13 comprises a sleeve-shaped syringe body, which surrounds a piston 13b and which is in sealing contact with the inner periphery of the syringe body. On its distal end, the syringe body comprises, in particular, an injection needle 13a, which is connected detachably to the syringe body and whose distal end is formed by the needle tip. Between the injection needle 13a and the piston 13b, a fluid product, in particular medication, is arranged within the syringe body, wherein the displacement of the piston 13b in a discharge direction, i.e., in the distal direction or toward the injection needle 13a, discharges the product through the hollow injection needle 13a from the product container 13. On its proximal end, the syringe body has a so-called finger flange, which protrudes radially outward over the periphery of the cylindrical syringe body.

The product container 13 is accommodated in a product container holder 1, referred to below as syringe holder 1, in such a manner that it is protected against being moved along the longitudinal axis L in the distal direction relative to the syringe holder 1. As can be seen in the example of FIG. 2a, the syringe holder 1 is connected by positive connection to the housing 2. The housing 2, for this purpose, has recesses into which the lock-in elements, formed here on the proximal end of the syringe holder 1, engage. The syringe holder 1 has at least one inward protruding shoulder 1b, against which is braced a tapering section of the product container 13, which is arranged distally with respect to the cylindrical syringe body section which guides the piston 13b.

The autoinjector comprises a dosing sleeve 5 which is arranged in the housing 2 and which is arranged, relative to the housing 2 and to a plunger rod 7, in a manner so it is rotationally fixed and axially movable. The dosing sleeve 5 is connected in a rotationally fixed and axially displaceable manner to a retaining ring 19, which is connected in a rotationally fixed and preferably axially fixed manner to the housing 2, in particular by snap connection.

In order to prevent the product container 13 from being able to be displaced relative to the syringe holder 1 in the proximal direction, the product container 13 is pressed on its proximal end by a holder spring section 5c formed by the retaining ring 19 into the engagement with the shoulder 1b. By means of the holder spring section 5c, longitudinal differences of the product container 13, which can occur due to manufacturing tolerances, can be compensated, wherein the firm seating of the product container 13 on the shoulder 1b is ensured.

The product container 13 is arranged, relative to the housing 2, in such a manner that the needle tip is distally beyond the distal end of the housing 2. In the initial or delivery state of the autoinjector, i.e., when the pull-off cap 4 is arranged on the autoinjector, the needle 13a is formed by a needle protection cap 14 which, in the depicted example, is referred to as a so-called rigid needle shield known to the person skilled in the art, alternatively known as a soft needle shield, in order to protect the needle 13a against soiling or to keep the needle 13a and the medication sterile. The rigid needle shield 14 is arranged on a needle holder section of the syringe body, wherein the tapering section of the syringe body is located between the needle holder section and the cylindrical section of the syringe body. The shoulder 1b is arranged between the syringe body and the proximal end of the rigid needle shield 14, in particular so that, between the rigid shield 14 and the shoulder 1b, a gap—albeit a small gap—is produced in order to prevent the shoulder 1b exerting a force on the rigid needle shield 14, whereby, for example, the sterility of the needle 13a and of the fluid product could be impaired. The pull-off cap 4 is snapped detachably to the housing 2 or a needle protection sleeve 3, wherein this snap connection is loosened, when the pull-up cap 4 is removed from the housing 2 or the needle protection sleeve 3. The pull-off cap 4 moreover comprises, in particular on a flexible arm, at least one catch 4b, which engages in a gap between the syringe body, in particular its tapering area, and the proximal end of the rigid needle shield 14. When the pull-off cap 4 is removed from the autoinjector, the catch 4b hooks into the proximal end of the rigid needle shield 14, as a result of which the rigid needle shield 14 is detached from the product container 13 and removed together with the cover cap 4 from the autoinjector (FIG. 3).

The autoinjector has a needle protection sleeve 3, which is displaceable relative to the housing 2 and along the longitudinal axis L by an actuation stroke $H_B$ in the proximal direction into an actuated position, in order to trigger a product discharge. In the initial position of the needle protection sleeve 3, as shown in FIGS. 6a, 6b, wherein the pull-off cap 4 is removed, the distal end of the needle protection sleeve 3 is distally beyond the needle tip of the needle 13a, so that access to the needle tip is at first prevented. By shifting the needle protection sleeve 3 by the actuation stroke $H_B$, the needle protection sleeve 3 is displaced in the proximal direction until the needle 13a protrudes from the distal end of the needle protection sleeve 3, in particular over a length that corresponds to the injection depth of the needle in the injection site. Preferably, the needle 13a should protrude beyond the distal end of the needle protection sleeve 3 by a distance such that a subcutaneous injection can occur. In particular, the housing 2 can form an abutment, with which the needle protection sleeve 3 is in contact in the actuated position.

After the injection has taken place, the needle protection sleeve 3 can be displaced, relative to the housing 2, from the actuated position along the longitudinal axis L by a needle protection stroke $H_N$ in the distal direction into a needle protection position (FIGS. 11a, 11b). In the needle protection position, the distal end of the needle protection sleeve 3 extends distally beyond the needle tip, so that access to the needle tip is prevented and the risk of injury is reduced. As described further below, the needle protection sleeve 3 can be blocked against being again pushed back out of the needle protection position.

The syringe holder 1 has a bevel 1a facing radially outward, wherein the beveling 1a engages in in a slit-shaped recess of the needle protection sleeve 3, which is arranged between the housing 2 and the syringe holder 1. In the initial position of the needle protection sleeve 3 (FIGS. 6a, 6b) and/or in the needle protection position of the needle protection sleeve 3 (FIGS. 11a, 11b), the needle protection sleeve 3, in particular the proximal end of the slit-shaped recess, is in contact with the bevel 1a, whereby a movement of the needle protection sleeve 3 in the distal direction is prevented. Into this slit-shaped recess, alternatively in another recess of the needle protection sleeve 3, a cam 1c, arranged resiliently on the syringe holder 1 and formed by the syringe holder 1, can engage. The cam 1c is designed so that, when an attempt is made to displace the needle protection sleeve 3 from the initial position into the actuated position, the cam 1c at first prevents the displacement of the needle protection sleeve 3, wherein the cam 1c is pressed out, when the force exerted on the needle protection sleeve 3 for pushing back exceeds a certain threshold value, whereby the needle protection sleeve 3 is abruptly pushed back into the actuated position. As a result, the needle 13a can be inserted abruptly into the insertion site. In order to insert the needle 13a or in order to displace the needle protection sleeve 3 into the actuated position, the distal end of the needle protection sleeve 3 is placed on the insertion site, wherein the housing 2 is then pressed in the direction of the insertion site, wherein, when the compressive force exceeds the above-mentioned threshold value, the housing 2 is displaced abruptly toward the insertion site, and the needle protection sleeve 3 is displaced relative to the housing 2 by the actuation stroke $H_B$ into the actuated position.

The autoinjector comprises a sleeve-shaped plunger rod 7 which forms, at its distal end, an inward protruding shoulder, against which a first spring 9 is braced, which can also be referred to as a discharge spring. The first spring 9 is arranged within the sleeve-shaped plunger rod 7. The first spring 9 is a compression spring acting as a coil spring that is sufficiently prestressed with energy in the initial or delivery state of the autoinjector, so that the product contained in the product container 13 can be discharged, in particular completely, by the displacement of the plunger rod 7 by a discharge stroke $H_A$, from the product container 13. In the delivery state of the device, there is a distance between the piston 13b and the distal end of the plunger rod 7, so that the plunger rod 7 strikes the piston 13b only during the performance of the priming stroke $H_P$, entraining said piston in the discharge direction. The first spring 9 is braced with its proximal end against a retaining element 6, which, in this example, has two arms 6c, wherein, on each arm 6c, a first engagement element 6a and a second engagement element 6b are arranged. The first engagement element 6a faces the longitudinal axis L radially, wherein the second engagement element 6b faces radially away from the longitudinal axis L. The first engagement element 6a engages in a first recess 7a formed by the plunger rod 7. In the delivery state of the autoinjector or before the performance of a priming, the proximal end of the first recess 7a is at a distance from the first engagement element 6a of the retaining element 6, which corresponds to the priming stroke $H_P$ (FIG. 2b). A locking sleeve 8, which can be shifted along the longitudinal axis L, holds the first engagement element 6a, in particular with its inner peripheral surface, in the engagement with the recess 7a of the plunger rod 7.

A sleeve-shaped displacement unit 11 comprises a flexible first engagement element 11a, which engages in a recess 17b of a sleeve-shaped mechanism holder 17, whereby the displacement unit 11 is axially fixed relative to the mechanism holder 17 as long as there is engagement. The mechanism holder 17 is snapped in an axially fixed and rotatable manner relative to the housing 2, in particular in an axially fixed and rotatable manner to the sleeve-shaped housing insert 12. The displacement unit 11 comprises a second engagement unit 11b, which engages in a second recess 7b of the plunger rod 7, whereby the plunger rod 7 is blocked by the second engagement unit 17b of the sleeve-shaped mechanism holder 17 from being moved in the distal direction. The sleeve-shaped housing insert 12 has a retaining surface 12d, with which the second engagement element 11b of the displacement unit 11 is in contact and which is held in engagement with the second recess 7b of the plunger rod 7.

On its outer periphery, the plunger rod 7 comprises a dose selection abutment 100 in the form of a protrusion. The dosing sleeve 5 comprises, distributed over its periphery, several, namely at least a first dosing abutment 110 (FIG. 2b) and a second dosing abutment 111 (FIG. 6b), which are angularly offset relative to one another about the longitudinal axis L and arranged along the longitudinal axis L in different axial positions. The dosing sleeve 5 comprises, in particular on its outer periphery, a stop abutment 5e, which is located at a distance opposite a stop counter-abutment 17a formed along the longitudinal axis L by the mechanism holder 17 (FIG. 2a).

For administering the medication, the pull-off cap 4 is removed together with the rigid needle shield 14 from the autoinjector (FIG. 3). Subsequently, the autoinjector is primed (FIGS. 4a, 4b). For this purpose, the dose setting element 16 is turned relative to the housing 2. The plunger rod 7 is connected, in particular via the retaining element 6, in a rotationally fixed manner to the dose setting element 16. The displacement unit 11 is connected in a rotationally fixed manner to the plunger rod 7 and the mechanism holder 17. The mechanism holder 17 in turn is connected in a rotationally fixed manner to the locking sleeve 8, wherein the locking sleeve 8 is connected in a rotationally fixed manner to a switching sleeve 15. When the dose setting element 16 is turned, the displacement unit 11 in particular is also turned, wherein the second engagement element 11b is turned from the operational engagement with the retaining surface 12d of the housing insert 12 which is rotationally fixed relative to the housing 2, wherein, in a position in which the second engagement unit 11b and the retaining surface 12d are angularly offset relative to one another about the longitudinal axis L, in particular in the first or second rotational position, the engagement element 11b of the displacement unit 11 is pushed out of the engagement with the second recess 7b of the plunger rod 7 due to the action of the prestressed discharge spring 9, in particular with a movement transverse to the longitudinal axis L (FIG. 4b). The prestressed discharge spring 9 displaces the plunger rod 7 by the priming stroke $H_P$ in the distal direction, until the proximal end of the first recess 7a of the plunger rod 7 strikes against the first engagement element 6a, as a result of which the movement of the plunger rod 7 in the distal direction is blocked. During the priming stroke $H_P$, the plunger rod 7 entrains the piston 13b, whereby the syringe 13 is primed (FIG. 5b).

Now the dose setting can occur (FIGS. 6a, 6b). For this purpose, the dose setting element 16 is turned into one of the several rotational positions such as, for example, the first or second rotational position relative to the housing 2. The plunger rod 7, the retaining element 6, the displacement unit 11, the mechanism holder 17, the locking sleeve 8, the switching sleeve 15, and a second spring 10 also turn with the dose setting element 16. In particular, by means of the turning of the dose setting element 16, the dose setting abutment 100 of the plunger rod 7 is turned relative to the first and second dosing abutments 110, 111 of the dosing sleeve 5. In the first rotational position of the dose setting element 16, the dose selection abutment 100 and the first dosing abutment 110 are arranged in alignment along the longitudinal axis L. In the second rotational position of the dose setting element 16, the dose selection abutment 100 is angularly offset about the longitudinal axis L toward the first dosing abutment 110 and in alignment with the second dosing abutment 111 (FIG. 6b).

In order to trigger the administration of the set product dose, i.e., in order to release the engagement of the first engagement unit 6a of the retaining element 6 from the recess 7a of the plunger rod 7, the needle protection sleeve 3 is displaced by the actuation stroke $H_B$ in the proximal direction into the housing 2. As a result, the proximal end 3a of the needle protection sleeve 3 entrains the switching sleeve 15, whereby the second spring 10, in particular the needle protection spring 10, is stressed. The switching sleeve 15 abuts, during its movement in the proximal direction, against the locking sleeve 8 and it also entrains the locking sleeve 8. Due to the movement of the locking sleeve 8 in the proximal direction, a first recess 8b of the locking sleeve 8 is displaced along the longitudinal axis L approximately into the position of the second engagement unit 6b, whereby the prestressed discharge spring 9 displaces the plunger rod 7 by a discharge stroke $H_A$ in the distal direction, whereby the first engagement unit 6a of the retaining element 6 is moved from the engagement with the recess 7a of the plunger rod 7 and at the same time the second engagement element 6b of the retaining element 6 is moved into the recess 8b of the locking sleeve 8, in particular with a movement transversely to the longitudinal axis L (FIG. 7a). Due to the movement of the locking sleeve 8 in the proximal direction, a second recess 8c of the locking sleeve 8 is displaced along the longitudinal axis L approximately into the position of a locking member 17c of the mechanism holder 17. The dose selection abutment 100 is moved toward the second dosing abutment 111 and past the first dosing abutment 110, until the dose selection abutment 100 strikes against the second dosing abutment 111 of the dosing sleeve 5, and entrains the dosing sleeve 5 at least over a distance, namely by the distance between the stop abutment 5e and the stop counter-abutment 17a of the mechanism holder 17, until the stop abutment 5e impacts against the stop counter-abutment 17a, as a result of which the movement of the dosing sleeve 5 in the distal direction and thus also the movement of the plunger rod 7 in the distal direction are blocked. Due to the movement of the dosing sleeve 5 in the distal direction, said dosing sleeve 5 is moved from the position in which it prevents the first engagement element 11a of the displacement unit 11 from being able to be displaced from the recess 17b of the mechanism holder 17 (FIG. 9b). Due to the movement of the dosing sleeve 5 in the distal direction, the dosing sleeve 5 presses the locking member 17c of the mechanism holder 17 into the second recess 8c of the locking sleeve 8, in particular with a movement transverse to the longitudinal axis L (FIG. 7a), whereby a movement of the locking sleeve 8 in the distal direction is blocked.

When the second engagement element 6b of the retaining element 6 engages with the recess 8b of the locking sleeve 8, the proximal end of the discharge spring 9 can accelerate the retaining element 6 in the proximal direction, wherein the engagement element 6b also accelerates the locking sleeve 8 in the proximal direction, wherein the locking sleeve 8, after the performance of a signal stroke $H_K$, strikes against the mechanism holder 17, and, as a result, a tactile and/or acoustic signal is generated (FIGS. 7a to 8b), signaling the beginning of the product discharge. In addition, by means of the second engagement element 6b, which is in engagement with the recess 8b of the locking sleeve 8, the movement of the locking sleeve 8 in the distal and proximal directions is blocked.

Since—as can be seen in FIGS. 9a, 9b—the blocking of the first engagement unit 11a of the displacement unit 11 by the dosing sleeve 5 at the end of the discharge $H_A$ is omitted, the stressed second spring 10, which is braced with its proximal end against a protrusion 11c of the displacement unit 11, can accelerate the displacement unit 11 in the proximal direction, wherein the first engagement unit 11a is released from the engagement with the first recess 17b. The displacement unit 11 is accelerated by a signal stroke $H_S$ in the proximal direction, until it abuts against the sleeve-shaped housing insert 12 and generates an acoustic and/or tactile signal, indicating the end of the product discharge. The movement of the displacement unit 11 in the proximal direction moreover has the effect that the displacement unit 11, in particular the protrusion 11c, is moved in a positive-locking rotation-preventing engagement with the housing 2 or the sleeve-shaped housing insert 12, whereby a turning of the displacement unit 11 relative to the housing 2 about the longitudinal axis L after the product discharge has occurred is prevented. Since the dose setting element 16 is connected in a rotationally fixed manner to the displacement unit 11, a turning of the dose setting element 16 relative to the housing 2 is blocked (FIG. 10a).

When the autoinjector is removed from the insertion site, the second spring 10 displaces the switching sleeve 15 relative to the housing 2 and/or the locking sleeve 8 in the distal direction, wherein the switching sleeve 15 displaces the needle protection sleeve 3 in the distal direction by the needle protection stroke $H_N$. Due to the engagement of the second engagement element 6b of the retaining element 6 with the recess 8b of the locking sleeve 8, the movement of the locking sleeve 8 in the distal and proximal directions is prevented, so that the switching sleeve 15 moves relative to the locking bar 8 and, at the end of the movement, is snapped in an axially fixed manner to the locking sleeve 8, in particular by means of a locking member 8a (FIG. 11c) of the locking sleeve 8 engaging in the switching sleeve 15, so that, when an attempt is made to displace the needle protection sleeve 3 in the proximal direction, this movement is blocked. In the process, the locking sleeve 8 is pressed against the mechanism holder 17, which is connected in an axially fixed manner to the housing 2 and which blocks the movement of the locking sleeve 8 in the proximal direction.

Second Embodiment

Figure 12:
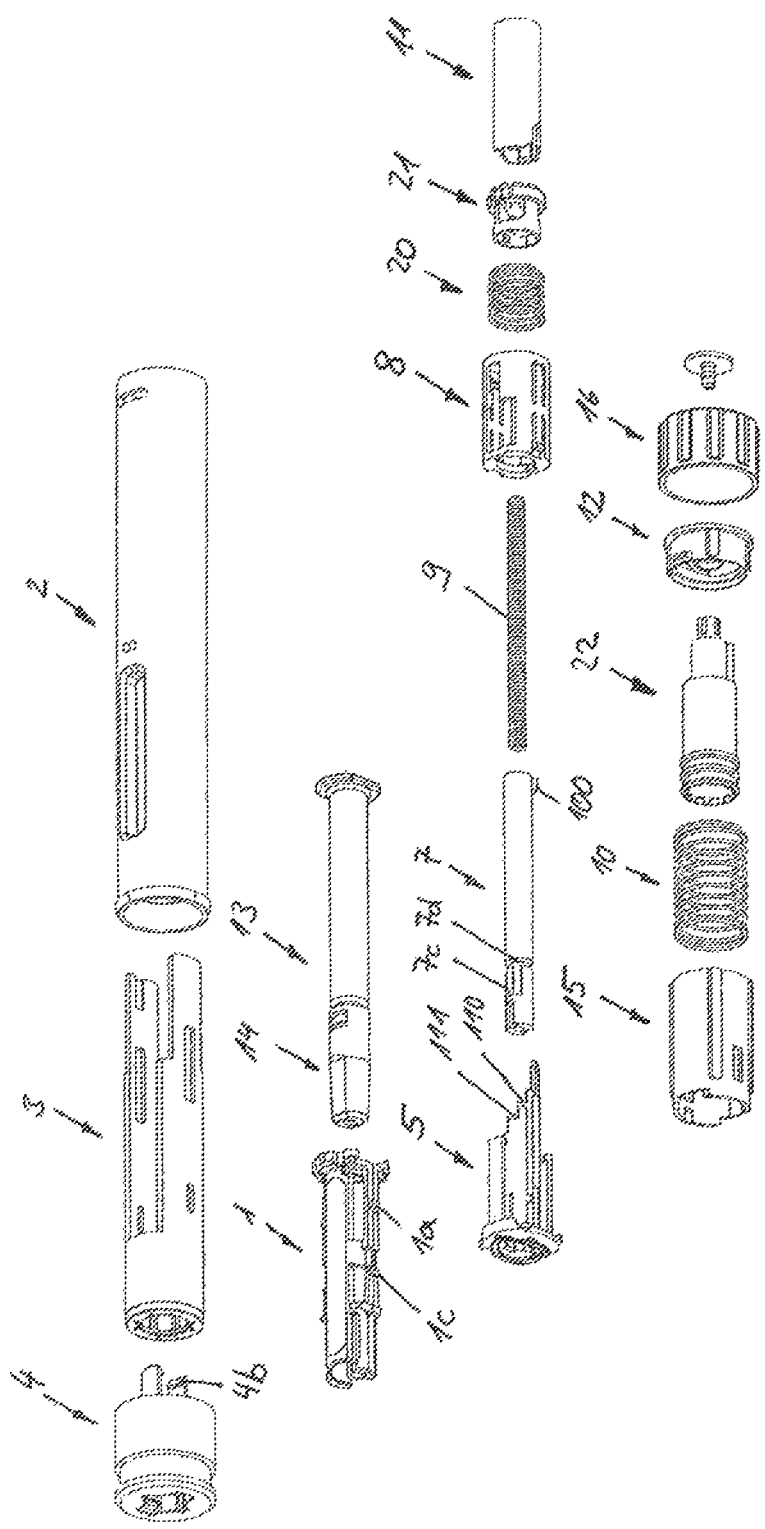
FIG. 12 shows an exploded view of an autoinjector according to a second embodiment.

In reference to FIGS. 12 to 22, the structural features and the function of the autoinjector according to the second embodiment are now described.

The autoinjector has a sleeve-shaped, elongate housing 2 with a longitudinal axis L, which, on its proximal end, comprises a sleeve-shaped housing insert 12, which is connected by positive lock to the housing 2 in a rotationally and axially fixed manner and arranged on the proximal end of the housing 2. The sleeve-shaped housing insert 12 has a lock-in catch. A dose setting element 16 comprises several, in particular at least two, or in accordance with the number of settable doses, lock-in grooves distributed over the periphery, wherein the lock-in catch engages in one of the lock-in grooves, and, when the dose setting element 16 is turned such as, for example, for a dose setting, it is moved from the lock-in groove and into another one of the lock-in grooves. As a result, quasi-stable lock-in positions are specified for the dose setting element 16.

The sleeve-shaped dose setting element 16 is connected, particularly by snap connection, on the proximal end of the housing 2 rotatably and in an axially fixed manner to the housing 2, forming, in particular, the proximal end of the autoinjector. The dose setting element 16 can be gripped by the user of the device and turned relative to the housing 2 by the muscle force of the user for setting a product dose to be discharged. For example, by means of the device, several doses can be set in different mL steps. For example, the dose setting element 16 can assume, relative to the housing, at least two quasi-stable rotational positions, or, in accordance with the number of settable doses, for example, eight different quasi-stable rotational positions, wherein, in a first rotational position, a first dose is set, and in a second rotational position, a second dose is set.

On the distal end of the autoinjector, in its delivery state (FIGS. 13a, 13b), a pull-off cap 4 is arranged, which is pulled or twisted off before the use of the autoinjector, and removed.

In the housing 2, a product container 13 in the form of a syringe is accommodated in a nondisplaceable manner relative to the housing 2—except for the installation of the autoinjector—along the longitudinal axis L. The product container 13 has a sleeve-shaped syringe body, which surrounds a piston 13b, which is in sealing contact on the inner periphery of the syringe body. The syringe body, on its distal end, comprises an injection needle 13a, which, in particular, is connected in an undetachable manner to the syringe body and whose distal end is formed by the needle tip. Between the injection needle 13a and the piston 13b, a liquid product, in particular medication, is arranged within the syringe body, wherein the displacement of the piston 13b in a discharge direction, i.e., in the distal direction or toward the injection needle 13a, discharges the product through the hollow injection needle 13a from the product container 13. The syringe body, on its proximal end, has a so-called finger flange, which protrudes radially outward over the periphery of the cylindrical syringe body.

The product container 13 is accommodated in a product container holder 1, hereafter referred to as syringe holder 1, in such a manner that it is protected at least against a movement along the longitudinal axis L in the distal direction relative to the syringe holder 1. The syringe holder 1, as can be seen in FIG. 13a, for example, is connected to the housing with a positive-lock connection, in particular engaged. For this purpose, the housing 2 has recesses, which engage in the lock-in elements formed here on the proximal end of the syringe holder 1. The syringe holder 1 has at least one inward protruding shoulder 1b, against which is braced a tapering section of the product container 13, which is arranged distally with respect to the cylindrical syringe body section guiding the piston 13b.

The autoinjector comprises a dosing sleeve 5, which is arranged in the housing 2 and which is arranged in a rotationally fixed manner and axially movable relative to the housing 2 and a plunger rod 7. The dosing sleeve 5 engages in a rotationally fixed and axially movable manner in the housing 2. The dosing sleeve 5 comprises an engagement element 6a, which is formed on an arm 6c of the dosing sleeve 5, in particular forming a single part, in such a manner that it can be deflected flexibly transversely to the longitudinal axis L. The engagement element 6a of the dosing sleeve 5 engages in a plunger rod 7 and blocks the plunger rod 7 against a movement in the distal direction. On the plunger rod 7, a prestressed first spring 9 acts, which applies or presses a force via the engagement element 6a on the dosing sleeve 5 pushing it in the distal direction in order to prevent the product container 13 being able to be displaced in the proximal direction relative to the syringe holder 1. The product container 13 is held on its proximal end by a retaining spring section 5c formed by the dosing sleeve 5 in engagement with the shoulder 1b.

The product container 13 is arranged, relative to the housing 2, in such a manner that the needle tip is distally beyond the distal end of the housing 2. In the initial or delivery state of the autoinjector, i.e., when the pull-off cap 4 is arranged on the autoinjector, the needle 13a is formed by a needle cover cap 14, which is referred to in the depicted example as a so-called rigid needle shield known to the person skilled in the art and alternatively referred to as soft needle shield, in order to protect the needle 13a against soiling or in order to keep the needle 13a and the medication sterile. The rigid needle shield 14 is arranged on a needle retaining section of the syringe body, wherein the tapering section of the syringe body is located between the needle retaining section and the cylindrical section of the syringe body. The shoulder 1b is arranged between the syringe body and the proximal end of the rigid needle shield 14, in particular in such a manner that, between the rigid needle shield 14 and the shoulder 1b, a gap—albeit a small gap—is provided in order to prevent the shoulder 1b exerting a force on the rigid needle shield 14, whereby, for example, the sterility of the needle 13a or of the fluid product could be impaired. The pull-off cap 4 is detachably connected by snap connection to the housing 2 or a needle protection sleeve 3, wherein this snap connection is released, when the pull-off cap 4 is removed from the housing 2 or the needle protection sleeve 3. The pull-off cap 4 moreover comprises, in particular, on a flexible arm, at least one catch 4b, which engages in a gap between the syringe body, in particular its tapering area, and the proximal end of the rigid needle shield 14. When the pull-off cap 4 is removed from the autoinjector, the catch 4b hooks into the proximal end of the rigid needle shield 14, as a result of which the rigid needle shield 14 is detached from the product container 13 and removed together with the cover cap 4 from the autoinjector (FIGS. 14a, 14b).

The autoinjector has a needle protection sleeve 3, which is displaceable relative to the housing 2 and along the longitudinal axis L by an actuation stroke $H_B$ (FIG. 19a) in the proximal direction into an actuated position, in order to trigger a product discharge. In the initial position of the needle protection sleeve 3, as shown in FIGS. 14a to 18b, wherein the pull-off cap 4 is removed, the distal end of the needle protection sleeve 3 is distally beyond the needle tip of the needle 13a, so that access to the needle tip is at first prevented. By displacing the needle protection sleeve 3 by the actuation stroke $H_B$, the needle protection sleeve 3 is displaced in the proximal direction until the needle 13a protrudes from the distal end of the needle protection sleeve 3, in particular over a length that corresponds to the injection depth of the needle into the injection site. Preferably, the needle 13a should protrude beyond the distal end of the needle protection sleeve 3 by a distance such that a subcutaneous injection can occur. In particular, the housing 2 can form an abutment, with which the needle protection sleeve 3 is in contact in the actuated position.

After the injection has taken place, the needle protection sleeve 3 can be displaced, relative to the housing 2, from the actuated position along the longitudinal axis L by a needle protection stroke $H_N$ in the distal direction into a needle protection position (FIG. 22). In the needle protection position, the distal end of the needle protection sleeve 3 extends distally beyond the needle tip, so that access to the needle tip is prevented and the risk of injury is reduced. As described further below, the needle protection sleeve 3 can be blocked against being pushed back again out of the needle protection position.

The syringe holder 1 has a bevel 1a facing radially outward, wherein the beveling 1a engages in in a slit-shaped recess of the needle protection sleeve 3, which is arranged between the housing 2 and the syringe holder 1. In the initial position of the needle protection sleeve 3 (FIGS. 14a to 18b) and/or in the needle protection position of the needle protection sleeve 3 (FIG. 22), the needle protection sleeve 3, in particular the proximal end of the slit-shaped recess, is in contact with the bevel 1a, whereby a movement of the needle protection sleeve 3 in the distal direction is prevented. Into this slit-shaped recess, alternatively in another recess of the needle protection sleeve 3, a cam 1c, arranged resiliently on the syringe holder 1 and formed by the syringe holder 1 can engage. The cam 1c is designed so that, when an attempt is made to displace the needle protection sleeve 3 from the initial position into the actuated position, the cam 1c at first prevents the displacement of the needle protection sleeve 3, wherein the cam 1c is pressed out, when the force exerted on the needle protection sleeve 3 for pushing back exceeds a certain threshold value, whereby the needle protection sleeve 3 is abruptly pushed back into the actuated position. As a result, the needle 13a can be inserted abruptly into the insertion site. In order to insert the needle 13a or in order to displace the needle protection sleeve 3 into the actuated position, the distal end of the needle protection sleeve 3 is placed on the insertion site, wherein the housing 2 is then pressed in the direction of the insertion site, wherein, when the compressive force exceeds the above-mentioned threshold value, the housing 2 is displaced abruptly toward the insertion site, and the needle protection sleeve 3 is displaced relative to the housing 2 by the actuation stroke $H_B$ into the actuated position.

The autoinjector comprises a sleeve-shaped plunger rod 7 which forms, at its distal end, an inward protruding shoulder, against which a first spring 9 is braced, which can also be referred to as a discharge spring. The first spring 9 is arranged within the sleeve-shaped plunger rod 7. The first spring 9 is a compression spring acting as a coil spring that is sufficiently prestressed with energy in the initial or delivery state of the autoinjector, so that the product contained in the product container 13 can be discharged, in particular completely, by the displacement of the plunger rod 7 by a discharge stroke $H_A$ from the product container 13. In the delivery state of the device, i.e., before a priming, there is a distance between the piston 13b and the distal end of the plunger rod 7, so that the plunger rod 7 strikes the piston 13b only during the performance of the priming stroke $H_P$, entraining said piston in the discharge direction. The first spring 9 is braced with its proximal end against a coupling sleeve 22, which is rotatable and axially fixed relative to the housing 2 and which is connected, in particular engaged, in a rotatable and axially fixed manner to the dose setting element 16.

The first engagement element 6a of the dosing sleeve 5 engages in a recess 7a, which is formed by the plunger rod 7. The recess 7a has a first abutment surface 7c and a second annular abutment surface 7d extending peripherally over the periphery of the plunger rod 7, the abutment surfaces being arranged with mutual angular offset along the longitudinal axis L, in particular with a distance corresponding approximately to the priming stroke $H_P$ (FIG. 15). The recess 7a comprises, in particular, a channel extending along the longitudinal axis L, which connects the first abutment surface 7c to the second abutment surface 7d of the plunger rod 7. In the delivery state of the autoinjector or before performing a priming, the engagement element 6a of the dosing sleeve 5 is in contact with the first abutment surface 7c of the plunger rod 7, as a result of which a movement of the plunger rod 7 in the distal direction is blocked. A locking sleeve 8, which can be displaced along the longitudinal axis L, in particular a retaining surface 8d formed by said locking sleeve 8, retains the first engagement element 6a of the dosing sleeve 5 in the engagement with the recess 7a of the plunger rod 7, in particular by blocking a movement of the first engagement member 6a transversely to the longitudinal axis L. The locking sleeve 8, in particular its retaining surface 8d, can be displaced from this position in the proximal direction into a position in which the locking sleeve 8, in particular its retaining surface 8d, releases the first engagement element 6a for a movement transverse to the longitudinal axis L.

By turning the dose setting element 16, the plunger rod 7 can be rotated relative to the dosing sleeve 5, as a result of which the first abutment surface 7c can be turned out of contact with the engagement element 6a of the dosing sleeve 5, as a result of which the plunger rod 7 can be displaced by means of the prestressed first spring 9 by the priming stroke $H_P$ in the distal direction, wherein the engagement element 6a of the dosing sleeve 5 is held during the priming stroke $H_P$ in the recess 7a, wherein, at the end of the priming stroke $H_P$, the engagement element 6a is in contact with the second abutment surface 7d, as a result of which the movement of the plunger rod 7 in the distal direction is blocked, in particular blocked until the product dose is set and its discharge has been started.

For the product discharge, the locking sleeve 8 can be displaced in the proximal direction, whereby its retaining surface 8d releases the engagement element 6a of the dosing sleeve 5 from the recess 7a or the engagement with the second abutment surface 7d, whereby the plunger rod 7 can be displaced by the first spring 9 in the distal direction or the displacement is released.

The plunger rod 7 comprises, on its outer periphery, a dose selection abutment 100 in the form of a protrusion. The dosing sleeve 5 comprises, distributed over its periphery, namely at least a first dosing abutment 110 (FIG. 12) and a second dosing abutment 111 (FIG. 12), which are angularly offset with respect to one another about the longitudinal axis L and arranged along the longitudinal axis L in different axial positions.

The autoinjector comprises a sleeve-shaped displacement unit 11, which is mounted in a rotationally fixed and axially displaceable manner on the dosing sleeve 5. The displacement unit 11 comprises, on its inner periphery, several entrainment abutments 11e, wherein, with each dosing abutment 110, 111 of the dosing sleeve 5, one of these entrainment abutments 11e is associated, wherein the respective entrainment abutment 11e, in relation to the dosing abutment 110, 111 with which it is associated, is prepositioned in proximal direction and positioned so that it is entrained by the dose selection abutment 100 of the plunger rod 7, when its dose abutment 110, 111 is in alignment with the dose selection abutment 100 and when the dose selection abutment 100 is moved toward the dosing abutment 110, 111. As a result, the displacement unit 11 is displaced in the distal direction, in particular toward the end of the discharge stroke $H_A$.

The autoinjector comprises a ring 21, which is rotatable about the longitudinal axis L and which surrounds the dosing sleeve 5. The ring 21 can be moved from a first position, in which it can be turned relative to the dosing sleeve 5 and is axially fixed at least in the proximal direction, into a second position, in which it is rotationally fixed relative to the dosing sleeve 5. The ring 21 comprises a protrusion, which is in contact with the shoulder of the dosing sleeve 5, wherein the shoulder blocks the movement of the ring 21 in the proximal direction and enables a turning of the ring 21. The ring 21 comprises a groove extending along the longitudinal axis L, into which the protrusion of the ring 21 can be turned with a turning axial movement, and which holds the protrusion of the ring by both sides, so that a rotation of the ring 21 relative to the dosing sleeve 5 is blocked.

The ring 21 is exposed to a force acting in the distal direction by means of a third prestressed spring 20, which is braced with its proximal end against the ring 21 and with its distal end against the dosing sleeve 5. When the ring 21 is turned out of the first position, i.e., out of the axially fixed engagement with the shoulder, the third spring 20 presses the ring 21 in the proximal direction, as a result of which the protrusion of the ring 21 is moved into the groove.

The displacement unit 11 comprises a transmission surface, which slides on a transmission counter-surface of the ring 21, when the displacement unit 11 is displaced in the distal direction, in particular toward the end of the product discharge, as a result of which the ring 21 is turned from the first position and displaced by translation by the second spring 20 into the second position.

The ring 21 can be accelerated or moved by the spring 20 against the coupling sleeve 22, wherein, when the ring 21 strikes against the coupling sleeve 22, a tactile and/or acoustic signal is generated, which signals the end of the discharge of the selected dose.

The ring 21 can be displaced by the spring 20 into a position, in particular the second position, in which the ring 21 engages in a rotationally fixed manner in the coupling sleeve 22, wherein the coupling sleeve 22 is coupled in a rotationally fixed manner to the dose setting element 16, in particular in a rotationally fixed engagement with said coupling sleeve, whereby the turning of the dose setting element 16 relative to the housing 2 is blocked.

The coupling sleeve 22 is coupled in a rotationally fixed manner to the plunger rod 7 via a detachable coupling engagement, at least before the triggering of the product discharge, i.e., when the engagement element 6a of the dosing sleeve 5 is in contact with the first abutment surface 7c and/or the second abutment surface 7d of the plunger rod 7. As a result, the plunger rod 7 can also be rotated along with the dose setting element 16 for the setting of the dose to be discharged. For this purpose, the proximal end of the plunger rod 7, in particular the protrusion with the dose selection abutment 100, and the coupling sleeve 22 engage in a rotationally fixed manner into one another. The coupling engagement can be released by means of a movement of the plunger rod 7 in the distal direction, i.e., in particular by means of the discharge stroke $H_A$, wherein the plunger rod 7 is displaced out of the engagement with the coupling sleeve 22 in the distal direction. When the coupling engagement is released, i.e., during the discharge of the dose or when the dose selection abutment 100 of the plunger rod 7 is in contact with one of the dosing abutments 110, 111 of the dosing sleeve 5, namely the selected dosing abutment, the dose setting element 16 and the plunger rod 7 are rotationally uncoupled from one another.

For the administration of the medication, the pull-off cap 4 together with the rigid needle shield 14 is removed from the autoinjector (FIG. 14a). Subsequently, the autoinjector is primed (FIG. 15) and the needle protection sleeve 3 is released for a movement in the proximal direction (FIG. 16). The needle protection sleeve 3 is blocked in the initial position from being displaced in the proximal direction. For this purpose, the needle protection sleeve 3, in particular its proximal end, strikes against the switching sleeve 15, wherein the switching sleeve 15 is blocked by a blocking abutment of the coupling sleeve 22 from being moved in the proximal direction.

After the removal of the pull-off cap 4, the dose setting element 16 is turned relative to the housing 2. The plunger rod 7 is connected in a rotationally fixed manner, in particular via the coupling sleeve 22, to the dose setting element 16.

By turning the dose setting element 16, the coupling sleeve 22, in particular, is also turned, wherein the coupling sleeve 22 is turned relative to the switching sleeve 15, so that the blocking abutment of the coupling sleeve 22 is turned out of the engagement with the switching sleeve 15. As a result, the switching sleeve 15 can be turned past the blocking abutment in the proximal direction.

Due to the turning of the dose setting element 16, the plunger rod 7, in particular, is turned relative to the dosing sleeve 5, as a result of which the engagement element 6a of the dosing sleeve 5 is turned out of contact with the first abutment surface 7c, so that the plunger rod 7 is moved by means of the prestressed spring 9, by the priming stroke $H_P$ in the distal direction, until the second abutment surface 7d of the plunger rod 7 abuts against the engagement element 6a of the dosing sleeve 5 and blocks the movement of the plunger rod 7 (FIG. 17).

Now the dose setting can occur (FIG. 18). For this purpose, the dose setting element 16 is turned into one of the several rotational positions such as, for example, the first or second rotational position relative to the housing 2. The plunger rod 7, the coupling sleeve 22 and the first spring 9 also turn with the dose setting element 16. In particular, by means of the turning of the dose setting element 16, the dose setting abutment 100 of the plunger rod 7 is turned relative to the first and second dosing abutments 110, 111 of the dosing sleeve 5, and the entrainment abutments 11e of the displacement unit 11. In the first rotational position of the dose setting element 16, the dose selection abutment 100 and the first dosing abutment 110 and the prepositioned entrainment abutment 11e associated with the first dosing abutment 110 are arranged in an alignment along the longitudinal axis L. In the second rotational position of the dose setting element 16, the dose selection abutment 100 is angularly offset about the longitudinal axis L toward the first dosing abutment 110 and in alignment with the second dosing abutment 111 and the prepositioned entrainment abutment 11e associated with the second dosing abutment 111.

In order to trigger the administration of the set product dose, i.e., in order to release the engagement of the first engagement element 6a from the recess 7a of the plunger rod 7, the needle protection sleeve 3 is displaced by the actuation stroke $H_B$ in the proximal direction into the housing 2. As a result, the proximal end 3a of the needle protection sleeve 3 entrains the switching sleeve 15, during a first and second partial stroke, into which the actuation stroke $H_B$ is subdivided.

The locking sleeve 8 comprises a catch 8e, which engages, in the initial position of the needle protection sleeve 3, in an axially fixed manner in the coupling sleeve 22, in particular in a first lock-in recess. The catch 8e can be moved transversely to the longitudinal axis L from the first lock-in recess, but it is prevented by a retaining surface of the switching sleeve 15 from moving out of the first lock-in recess (FIGS. 14*b*, 16).

During the first partial stroke, the switching sleeve 15 is moved relative to the locking sleeve 8 and the coupling sleeve 22, whereby a recess 15*a* is moved relative to the longitudinal axis L into the position of the catch 8*e* of the locking sleeve 8, so that the lateral blocking of the catch 8*e* is released. During the second partial stroke, the needle protection sleeve 3 also entrains the locking sleeve 8. The locking sleeve 8 moves in the proximal direction relative to the coupling sleeve 22. An abutment 3*c* of the needle protection sleeve 3 strikes against a locking member 8*a* of the locking sleeve 8 and entrains the locking sleeve 8. The catch 8*e* of the locking sleeve 8 is disengaged from the first lock-in recess and engaged in a second lock-in recess of the coupling sleeve 22. As a result, a locking of the needle protection sleeve 3 is arranged. During the actuation stroke $H_B$, a second spring 10, in particular a needle protection spring is stressed.

Due to the movement of the locking sleeve 8 in the proximal direction, the retaining surface 8*d* is displaced along the longitudinal axis L out of the lateral position, in which it blocks the movement of the engagement element 6*a* of the dosing sleeve 5 out of the recess 7*a* of the plunger rod 7. Thereby, the prestressed discharge spring 9 can displace the plunger rod 7 by the discharge stroke $H_A$ in the distal direction. The engagement element 6*a* is pressed out of the engagement with the recess 7*a* with a movement transverse to the longitudinal axis L (FIG. 19*a*).

During the discharge stroke $H_A$, the plunger rod 7 is displaced in the distal direction until the rotationally fixed engagement between plunger rod 7 and coupling unit 22 is released.

The dose selection abutment 100 of the plunger rod 7 is moved toward the second dosing abutment 111, wherein the dose selection abutment 100, toward the end of the discharge stroke $H_A$, entrains the entrainment abutment 11*e* of the displacement unit 11 which is prepositioned and associated with the second dosing abutment 111, at least over a distance such that the displacement unit 11 is displaced relative to the dosing sleeve 5 in the distal direction, until the dose selection abutment 100 strikes the second dosing abutment 111, whereby the movement of the plunger rod 7 in the distal direction is blocked. During the discharge stroke $H_A$, the dose selection abutment 100 of the plunger rod 7 is moved past the first dosing abutment 110.

Due to the movement of the displacement unit 11 in the distal direction, it slides on the ring 21 and turns it out of its first position (FIG. 20), as a result of which the ring 21 is pressed by the spring 20 into its second position, and, in the process, on the one hand, a signal is generated and, on the other hand, a coupling sleeve 22 is coupled in a rotationally fixed manner to the dosing sleeve 5, as a result of which the dose setting element 16 is rotationally fixed relative to the housing 2 and thus a dose setting can no longer be carried out (FIG. 21).

When the autoinjector is removed from the insertion site, the second spring 10 displaces the switching sleeve 15 relative to the housing 2 and/or the locking sleeve 8 in the distal direction, wherein the switching sleeve 15 displaces the needle protection sleeve 3 in the distal direction by the needle protection stroke $H_N$, whereby the locking member 8*a* of the locking sleeve 8 is engaged in the switching sleeve 15, in particular the recess 15*a*, and the switching sleeve 15 blocks the disengagement of the catch 8*e* of the locking sleeve 8 from the second lock-in recess of the coupling sleeve 22.

Due to the engagement of the locking member 8*a* of the locking sleeve 8 in the recess 15*a* of the switching sleeve 15 and the engagement of the catch 8*e* of the locking sleeve 8 in the coupling sleeve 22, the locking sleeve 8 and the switching sleeve 15 are prevented from moving in the distal direction, so that, when an attempt is made to displace the needle protection sleeve 3 in the proximal direction, this movement is blocked.

Third Embodiment

Figure 23:
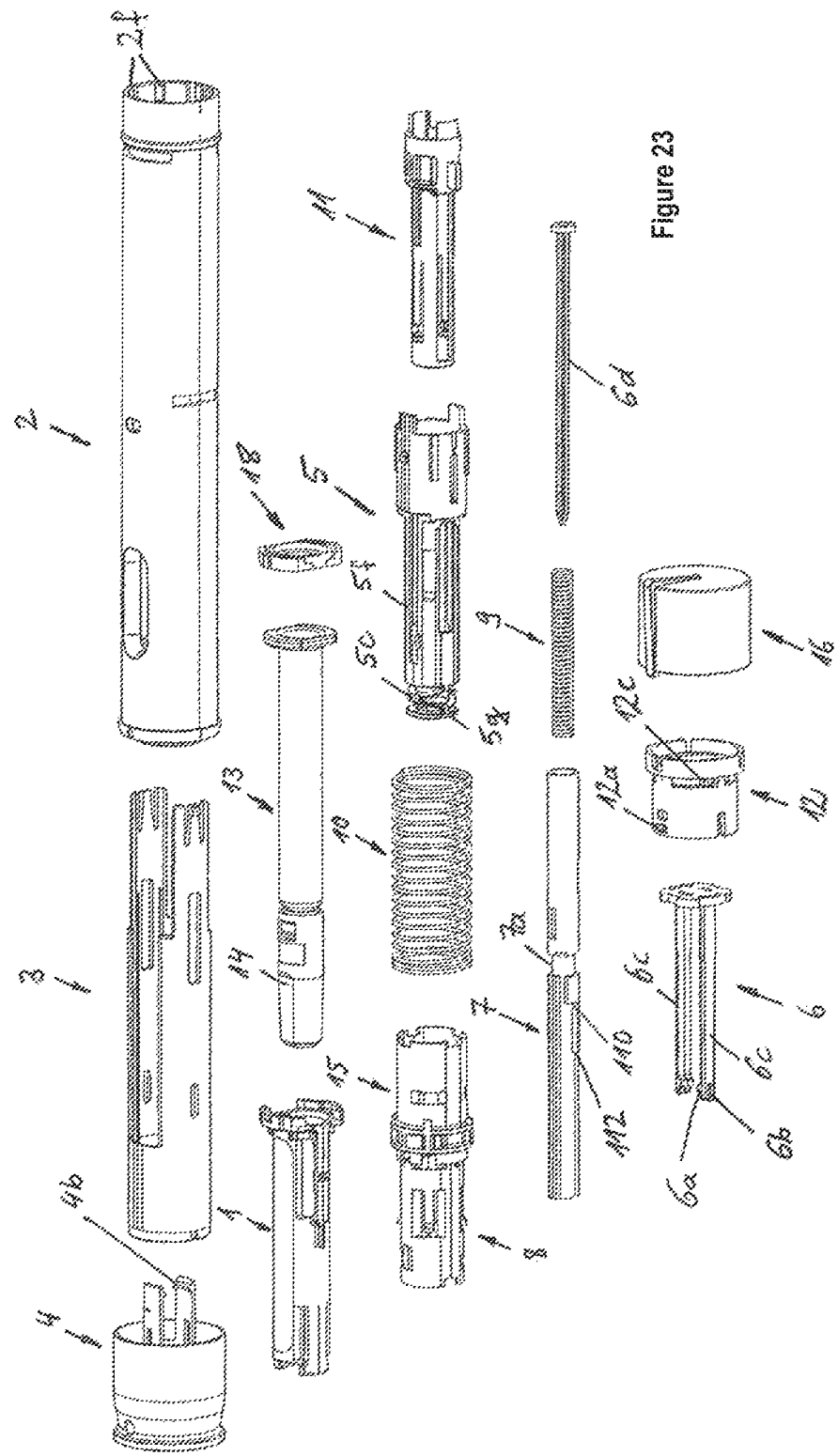
FIG. 23 shows an exploded view of an autoinjector according to a third embodiment.

In reference to FIGS. 23 to 32*b*, the structural features and the function of the autoinjector according to the third embodiment are now described.

The autoinjector comprises a sleeve-shaped, elongate housing 2 with a longitudinal axis L, which, at its proximal end, comprises a sleeve-shaped housing insert or rotation sleeve 12, which is connected with positive connection to the housing 2 in a rotational and axially fixed manner and which is arranged on the proximal end of the housing 2. The rotation sleeve 12 is snapped by means of a protrusion 12*a* with a snap into a recess 2*a* of the housing 2, so that it is rotatable and axially fixed relative to the housing 2 and, in particular, so that it cannot be removed from the housing 2, or so that it cannot be removed in a simple way. The rotation sleeve 12 comprises a lock-in catch 12*c*. The housing 2 comprises several, in particular at least two, lock-in grooves 2*f* distributed over the periphery, wherein the lock-in catch 12*c* engages in one of the lock-in grooves 2*f* and, when the rotation sleeve 12 is turned, such as, for example, for a dose setting, is moved out of the lock-in groove 2*f* and moved into another of the lock-in grooves 2*f*. As a result, quasi-stable lock-in positions are specified for the rotation sleeve 12, and a dose setting element 16 connected in rotationally fixed manner to the rotation sleeve 12 is specified.

The sleeve-shaped dose setting element 16 is connected on the proximal end of the housing 2 rotatably and in an axially fixed manner to the housing, forming, in particular, the proximal end of the autoinjector. The dose setting element 16 can be gripped by the user of the device and turned relative to the housing 2 for the setting of a product dose to be discharged. For example, it is possible to set two different doses to be discharged, such as, for example, 0.25 and 0.5 mL. Alternatively, the lock-in catch 12*c* can be arranged on the dose setting element 16. For example, the dose setting element 16 can assume, relative to the housing 2, at least three different quasi-stable rotational positions, wherein no dose can be set in an initial position, a first dose can be set in a first position, and a second dose can be set in a second position, etc.

On the distal end of the autoinjector, in its delivery state (FIGS. 24*a*-24*c*), a pull-off cap 4 is arranged, which is pulled or twisted off before the use of the autoinjector, and removed.

In the housing 2, a product container 13, in the form of a syringe, is accommodated non-displaceably relative to the housing 2—except for the installation of the autoinjector—along the longitudinal axis L. The product container 13 comprises a sleeve-shaped syringe body that surrounds a piston 13*b* and is in sealing contact with the inner periphery of the syringe body. On its distal end, the syringe body comprises, in particular, an injection needle 13*a*, which is connected detachably to the syringe body and whose distal end is formed by the needle tip. Between the injection needle 13a and the piston 13b, a fluid product, in particular medication, is arranged within the syringe body, wherein the displacement of the piston 13b in a discharge direction, i.e., in the distal direction or toward the injection needle 13a, causes the discharge of the product through the hollow injection needle 13a from the product container 13. On its proximal end, the syringe body comprises a so-called finger flange, which protrudes radially outward over the periphery of the cylindrical syringe body.

The product container 13 is accommodated in a product container holder 1, referred to below as syringe holder 1, in such a manner that it is protected at least against movement along the longitudinal axis L in the distal direction relative to the syringe holder 1. As can be seen in FIG. 24a, for example, the syringe holder 1 is connected by positive connection to the housing 2. For this purpose, the housing 2 has recesses into which the lock-in elements, formed here on the proximal end of the syringe holder 1, engage. The syringe holder 1 has at least one inward protruding shoulder 1b, against which is braced a tapering section of the product container 13, which is arranged distally with respect to the cylindrical syringe body section, which guides the piston 13b.

The autoinjector comprises a dosing sleeve 5, which is arranged in the housing 2 and which is snapped to the housing 2 or to a sleeve-shaped housing insert in a manner so that it is rotatable and preferably axially fixed relative to the housing 2 and a plunger rod 7, in particular in a manner so that it is axially fixed to the housing or to the sleeve-shaped housing insert.

In order to prevent the product container 13 from being able to be displaced relative to the syringe holder 1, the product container 13 is pressed at its proximal end by a retaining spring section 5c, which acts via a rotation prevention sleeve 18 on the syringe body, into engagement with a shoulder 1b. Due to the retaining spring section 5c, length differences of the product container 13, which can occur due to manufacturing tolerances, can be compensated, wherein the firm seating of the product container 13 on the shoulder 1b is ensured.

The product container 13 is arranged, relative to the housing 2, in such a manner that the needle tip extends distally beyond the distal end of the housing 2. In the initial or delivery state of the autoinjector, i.e., when the pull-off cap 4 is arranged on the autoinjector, the needle 13a is formed by a needle protection cap 14 which, in the depicted example, is referred to as a so-called rigid needle shield known to the person skilled in the art, alternatively known as a soft needle shield, in order to protect the needle 13a against soiling or to keep the needle 13a and the medication sterile. The rigid needle shield 14 is arranged on a needle holder section of the syringe body, wherein the tapering section of the syringe body is located between the needle holder section and the cylindrical section of the syringe body. The shoulder 1b is arranged between the syringe body and the proximal end of the rigid needle shield 14, in particular so that between the rigid needle shield 14 and the shoulder 1b, a gap—albeit a small gap—is produced in order to prevent the shoulder 1b exerting a force on the rigid needle shield 14, whereby, for example, the sterility of the needle 13a and of the fluid product could be impaired. The pull-off cap 4 is snapped detachably to the housing 2 or a needle protection sleeve 3, wherein this snap connection is loosened, when the pull-off cap 4 is removed from the housing 2 or the needle protection sleeve 3. The pull-off cap 4 moreover comprises, in particular on a flexible arm, at least one catch 4b, which engages in a gap between the syringe body, in particular its tapering area, and the proximal end of the rigid needle shield 14. When the pull-off cap 4 is removed from the autoinjector, the catch 4b hooks into the proximal end of the rigid needle shield 14, as a result of which the rigid needle shield 14 is detached from the product container 13 and removed together with the cover cap 4 from the autoinjector (FIG. 25).

The autoinjector has a needle protection sleeve 3, which is displaceable relative to the housing 2 and along the longitudinal axis L by an actuation stroke $H_B$ in the proximal direction into an actuated position, in order to trigger a product discharge. In the initial position of the needle protection sleeve 3 as shown in FIGS. 26a-26b, wherein the pull-off cap 4 is removed, the distal end of the needle protection sleeve 3 is distally beyond the needle tip of the needle 13a, so that access to the needle tip is at first prevented. A catch 3b on the needle protection sleeve 3 is engaged in a recess 2b of the housing 2. By displacing the needle protection sleeve 3 (FIGS. 26b-27a) by the actuation stroke $H_B$, the catch 3b is pressed out of the recess 2b of the housing 2, and the needle protection sleeve 3 is displaced in the proximal direction until the needle 13a protrudes from the distal end of the needle protection sleeve 3, in particular over a length that corresponds to the injection depth of the needle into the injection site. Preferably, the needle 13a should protrude beyond the distal end of the needle protection sleeve 3 by a distance such that a subcutaneous injection can occur. In particular, the housing 2 can form an abutment with which the needle protection sleeve 3 is in contact in the actuated position.

After the injection has taken place, the needle protection sleeve 3 can be displaced, relative to the housing 2, from the actuated position along the longitudinal axis L by a needle protection stroke $H_N$ in the distal direction into a needle protection position (FIGS. 32a-32b). In the needle protection position, the distal end of the needle protection sleeve 3 extends distally beyond the needle tip, so that access to the needle tip is prevented and the risk of injury is reduced. As described further below, the needle protection sleeve 3 can be blocked against being pushed back again out of the needle protection position.

The syringe holder 1 has a bevel 1a facing radially outward, wherein the bevel 1a engages in a slit-shaped recess of the needle protection sleeve 3, which is arranged between the housing 2 and the syringe holder 1. In the initial position of the needle protection sleeve 3 (FIGS. 24a-24c) and/or in the needle protection position of the needle protection sleeve 3 (FIGS. 32a-32b), the needle protection sleeve 3, in particular the proximal end of the slit-shaped recess, is in contact with the bevel 1a, whereby a movement of the needle protection sleeve 3 in the distal direction is prevented. Into this slit-shaped recess, alternatively into another recess of the needle protection sleeve 3, a cam, which is arranged resiliently on the syringe holder 1 and formed by the syringe holder 1, can engage. The catch 3b on the needle protection sleeve 3 is engaged in the recess 2b of the housing, in such a manner that, when an attempt is made to displace the needle protection sleeve 3 from the initial position into the actuated position, the catch 3b at first prevents the displacement of the needle protection sleeve 3, wherein the catch 3b is pressed out of the recess 2b, when the force exerted on the needle protection sleeve 3 in order to push it back exceeds a certain threshold value, as a result of which the needle protection sleeve 3 is pushed back abruptly into the actuated position (FIGS. 26b-27a). As a result, the needle 13a can be inserted abruptly into the insertion site. In order to insert the needle 13a or in order to displace the needle protection sleeve 3 into the actuation position, the distal end of the needle protection sleeve 3 is placed on the insertion site, wherein the housing 2 is then pressed in the direction of the insertion site, wherein, when the compressive force exceeds the above-mentioned threshold value, the housing 2 is displaced abruptly toward the insertion site, and the needle protection sleeve 3 is displaced relative to the housing 2 by the actuation stroke $H_B$ into the actuated position.

The autoinjector moreover comprises a sleeve-shaped plunger rod 7, which forms an inward protruding shoulder, against which a first spring 9 is braced, which can also be referred to as a discharge spring. The first spring 9 is arranged within the sleeve-shaped plunger rod 7. The first spring 9 is a compression spring acting as a coil spring, which is sufficiently prestressed with energy in the initial or delivery state of the autoinjector, so that the product contained in the product container 13 can be discharged, in particular completely, by the displacement of the plunger rod 7 by a discharge stroke $H_A$ from the product container 13. In the delivery state of the device, there is a distance between the piston 13*b* and the distal end of the plunger rod 7, so that the plunger rod 7 strikes the piston 13*b* only at the time of the performance of the discharge stroke $H_A$, entraining said piston in the discharge direction.

The first spring 9 is braced with its proximal end against a retaining element 6, which, in this example, has two arms 6*c*, wherein, on each arm 6*c*, a first engagement element 6*a* and a second engagement element 6*b* are arranged. The first engagement element 6*a* faces radially towards the longitudinal axis L, wherein the second engagement element 6*b* faces radially away from the longitudinal axis L. The first engagement element 6*a* engages in a first recess 7*a* formed by the plunger rod 7, whereby a movement of the plunger rod 7 relative to the retaining element 6 in the distal direction or in the discharge direction is prevented. As a result, the first spring 9 is retained in its stressed state. Within the first spring 9, a guide pin 6*d* is arranged, which is inserted through the proximal end of the of the first spring 9 into the core of the spring 9, and which comprises, on its proximal end, a head against which the first spring 9 is braced with its proximal end. The head of the guide pin 6*d* lies loosely against the retaining element 6, so that the retaining element 6 can be turned relative to the guide pin 6*d*. The guide pin 6*d* prevents a lateral deflection of the first spring 9 during and at the end of the discharge stroke $H_A$ of the plunger rod 7.

The autoinjector comprises a switching module 8, 15, which comprises a switching sleeve 15 and a locking sleeve 8 surrounded by the switching sleeve 15. In the delivery state of the device, the first engagement element 6*a* of the retaining element 6 is retained by the inner periphery of the locking sleeve 8, which is in contact with the second engagement element 6*b* of the retaining element 6, in the engagement with the first recess 7*a* of the plunger rod 7.

The switching sleeve 15 is connected to the proximal end 3*a* of the needle protection sleeve 3 or is at least in contact with the proximal end 3*a* of the needle protection sleeve 3. A second spring 10, within which the first spring 9 is arranged and which preferably at least partially surrounds the switching sleeve 15 and the locking sleeve 8, is braced with its distal end against the switching sleeve 15. Part of the switching sleeve 15 is thus arranged between the needle protection sleeve 3 and the distal end of the second spring 10. The second spring 10 is a spring made of metal acting as a compression spring and designed as a coil spring. The second spring 10 is braced with its proximal end against a displacement unit 11, in particular against a protrusion 11*c*, which engages in an axially displaceable and rotationally fixed manner in the dosing sleeve 5, in particular through a slit-shaped groove 5*b* of the dosing sleeve 5. The second spring 10 thus also surrounds the dosing sleeve 5 at least partially, preferably completely.

The switching sleeve 15 comprises a recess 15*a*, into which a locking member 8*a* of the locking sleeve 8 engages. The locking member 8*a* is saw tooth-shaped and protrudes radially away from the longitudinal axis L. The locking member 8*a* is resiliently arranged on an arm, which is formed by the locking sleeve 8. Due to the displacement of the switching sleeve 15 in the proximal direction, the locking sleeve 8 is entrained via the engagement of the locking member 8*a* in the proximal direction.

By displacing the needle protection sleeve 3 into the actuated position, the switching sleeve 15 is also entrained by the actuation stroke $H_B$, as a result of which the second spring 10 is stressed. If the needle protection sleeve 3 is not displaced completely into the actuated position, the second spring 10 can displace the switching sleeve 15 and the needle protection sleeve 3 back again into the initial position, wherein, via the engagement of the locking member 8*a*, the locking sleeve 8 is also entrained by the switching sleeve 15.

The displacement unit 11, which is in particular sleeve-shaped, in the delivery state or before the triggering of the product discharge, is in an axially fixed engagement with the plunger rod 7. The displacement unit 11 comprises a first engagement unit 11*a*, which engages in a recess 7*b* of the plunger rod 7, as well as a second engagement element 11*b*. The first engagement element 11*a* and the second engagement element 11*b* are resiliently arranged on the end of an arm 11*d* of the displacement unit 11. The displacement unit 11 comprises two such arms 11*d* with a first engagement element 11*a* and a second engagement element 11*b*. The first engagement element 11*a* faces radially toward the longitudinal axis L, wherein the second engagement element 11*b* faces radially away from the longitudinal axis L. In the delivery state, the first engagement element 11*a* is retained by the inner periphery of the locking sleeve 8 in the axially fixed engagement with the plunger rod 7. The second engagement element 11*b* is in contact with the inner periphery of the locking sleeve 8. The rotation sleeve 12 comprises a signal abutment 12*b*, against which the displacement unit 11 can strike in order to generate a signal and which is preferably in contact with the displacement unit 11 in the delivery state of the device.

The rotation prevention sleeve 18, which is preferably displaceable along the longitudinal axis L, connects the housing 2 and the plunger rod 7 in a rotationally fixed manner, wherein the plunger rod 7 is displaceable relative to the rotation prevention sleeve 18 along the longitudinal axis L. The plunger rod 7, on its outer periphery, comprises a first dosing abutment 110 and optionally a retaining abutment 112.

At least the dose setting element 16 and the dosing sleeve 5 are connected in a rotationally fixed manner, so that a turning of the dose setting element 16 produces a turning of the dosing sleeve 5. In the depicted example, the dose setting element 16 is connected in a rotationally fixed manner to the dosing sleeve 5, the displacement unit 11, the retaining element 6, the switching sleeve 15, the locking sleeve 8 and the second spring 10, so that a turning of the dose setting device 16 produces a turning of the dosing sleeve 5, the displacement unit 11, the retaining element 6, the switching sleeve 15, the locking sleeve 8 and the second spring 10.

The dosing sleeve 5, particularly a retaining section 5g forming the distal end of the dosing sleeve 5 and that is resiliently connected, in a manner so as to form a single part, via the retaining spring section 5c to a main section 5f of the dosing sleeve 5, comprises a dose selection abutment 100. In the initial position, at least when no dose can be set by means of the dose setting element 16, the optionally present retaining abutment 112 can be in contact with the dose selection abutment 100, in order to remove the force of the prestressed first spring 9 from the discharge mechanism of the autoinjector during longer storage periods.

By turning the dose setting element 16 for the setting of the product dose to be administered, the dose setting abutment 100 of the dosing sleeve 5 can be turned relative to the first dosing abutment and the optionally present retaining abutment 112 about the longitudinal axis L.

In the initial position of the autoinjector, a catch 3b of the needle protection sleeve 3 engages in a recess of the housing 2 (FIG. 24b). The switching sleeve 15 has a retaining surface 15b, which is arranged, relative to the catch 3b, in such a manner that it prevents the catch 3b from moving out of the recess. In order to be able to displace the needle protection sleeve 3 into the proximal direction, it is necessary to release the blocking of the movement out of the recess of the housing 2 and enable movement of the catch 3b out of the recess.

In order to administer the product from the product container 13, the pull-off cap 4 together with the rigid needle shield 14 (FIG. 25) is removed from the autoinjector. Subsequently or before, by turning the dose setting element 16 relative to the housing, a dose to be discharged is set. By turning the dose setting element 16 out of the initial position, in which the retaining abutment 112 is in contact with the dose selection abutment 100, into a first rotational position for a first dose and into a second rotational position for a second dose, the retaining surface 15b is turned relative to the catch 3b of the needle protection sleeve 3 into a position in which the catch 3b can move out of the recess.

When the dose setting element 16 assumes its first rotational position of the at least two rotational positions, the dose selection abutment 100 is arranged in alignment along the longitudinal axis L with the first dosing abutment 110.

When the dose setting element 16 assumes its second rotational position of the at least two rotational positions, the dose selection abutment 100 is arranged with angular offset about the longitudinal axis L with respect to the first dosing abutment 110.

The distal end of the needle protection sleeve 3 is placed on the insertion site of a patient, where the housing 2 is displaced towards the insertion site, whereby the needle protection sleeve 3 is moved from its initial position by the actuation stroke $H_B$ in the proximal direction relative to the housing 2 into the actuated position (FIGS. 26a,b and 27a,b). In the process, the catch 3b of the needle protection sleeve 3 is pressed out of the housing 2. The second spring 10 is stressed, wherein the switching sleeve 15 is entrained by the needle protection sleeve 3 by the actuation stroke $H_B$. The locking sleeve 8 comprises a first recess 8b, which is moved, by displacement of the locking sleeve 8 by the actuation stroke $H_B$ along the longitudinal axis L, into the position of the second engagement element 6b of the retaining element 6, as represented in FIGS. 27a,b. Thereby, the first engagement element 6a is moved out of the engagement with the plunger rod 7 with a movement transverse to and away from the longitudinal axis L, wherein, at the same time, the second engagement element 6b of the retaining element 6 is moved into the engagement with the locking sleeve 8, in particular its first recess 8b. As a result, the plunger rod 7 is released for the movement by the discharge stroke $H_A$ in the discharge direction (FIG. 28), wherein the size of the discharge stroke $H_A$ depends on the rotational position of the dose setting element 16.

When the dose setting element 16 is in its first rotational position, the first dosing abutment 110 of the plunger rod 7 is moved toward the dose selection abutment 100 of the dosing sleeve 5 until it strikes against the dose selection abutment 100, whereby the discharge movement of the plunger rod 7 is stopped and only a true partial quantity of the product in the product container 13 is expelled.

When the dose setting element 16 is in its second rotational position, the first dosing abutment 110 of the plunger rod 7, which is arranged with angular offset about the longitudinal axis L with respect to the dose selection abutment 100 of the dosing sleeve 5, is moved past the dose selection abutment 100 along the longitudinal axis L. In the process, the discharge stroke $H_A$ is greater than in the first rotational position of the dose setting element 16. In the depicted example, the piston 13b is displaced in the product container 13 until it strikes against the tapering area of the syringe body, whereby the discharge movement of the plunger rod 7 is stopped, and the entire product quantity contained in the product container 13 is expelled. Alternatively, a second dosing abutment (not shown) can be formed on the plunger rod 7 and be angularly offset with respect to the first dosing abutment 110 of the plunger rod 7 about the longitudinal axis L and arranged along the longitudinal axis L in another position, wherein, in the second rotational position of the dose setting element 16, the dose selection abutment 100 of the dosing sleeve 5 is arranged in alignment along the longitudinal axis L with the second dosing abutment. The second dosing abutment is then moved toward the dose selection abutment 100 of the dosing sleeve 5 until it strikes against the dose selection abutment 100, whereby the discharge movement of the plunger rod 7 is stopped and only a true partial quantity, which is greater than the partial quantity when the dose setting element is in its first rotational position, is expelled. Analogously to this alternative, in a development, the dose setting element 16 can be turned into a third rotational position, in which a third dosing abutment of the plunger rod 7 and the dose selection abutment 100 of the dosing sleeve 5 are in alignment, etc.

When the plunger rod 7 is released for the movement by the discharge stroke $H_A$ into the discharge direction (FIG. 28), the axially fixed coupling between the plunger rod 7 and the retaining element 6 is eliminated, whereby the retaining element 6, which can be moved over at least a distance relative to the housing 2 and along the longitudinal axis L, can be moved by the first spring 9 in the proximal direction, wherein the retaining element 6, via the engagement of the second engagement element 6b in the recess 8b of the locking sleeve 8, entrains the locking sleeve 8 by a start signal stroke, whereby the locking sleeve 8 strikes against a start signal abutment, which is formed by the dosing sleeve 5, and thereby issues an acoustic and/or tactile signal signaling to the user of the device that the product discharge has started. By displacing the locking sleeve 8 by the actuation stroke $H_B$, the locking member 8a of the locking sleeve 8 is released for a movement transverse to and toward the longitudinal axis L, since the dosing sleeve 5 has a recess 5d, which enables such a movement of the locking member 8a of the locking sleeve 8 when the locking sleeve 8 has been displaced by the actuation stroke $H_B$ or when the needle protection sleeve 3 is in its actuated position (FIG. 27b).

Since the displacement unit 11 is still connected in an axially fixed manner to the plunger rod 7, it is entrained by a first partial stroke of the discharge stroke $H_A$ in the discharge direction, wherein the displacement unit 11 is moved by approximately the first partial stroke away from the signal abutment 12b, as can be seen best in FIG. 29. At the end of the first partial stroke, during which the first and second engagement units 11a, 11b of the displacement unit 11 are moved relative to the locking sleeve 8, the first engagement element 11a is pressed out of the engagement with the plunger rod 7, wherein, at the same time, the second engagement element 11b is moved into the second recess 8c of the locking sleeve 8 with a movement transverse to the longitudinal axis L and radially away from the longitudinal axis L (FIG. 29). As a result, the displacement unit 11 is prevented from moving in the proximal direction relative to the housing 2 or the locking sleeve 8. The second engagement unit 11b is held by the outer periphery of the plunger rod 7 in the engagement with the recess 8c of the locking sleeve 8, when the plunger rod 7 is moved by a second partial stroke of the discharge stroke $H_A$. The outer peripheral surface of the plunger rod 7 retains the second engagement element 6b of the retaining element 6 in the engagement with the first recess 8b of the locking sleeve 8. At the end of the discharge stroke $H_A$, the piston rod 7 releases the second engagement unit 11b of the displacement unit 11 from the engagement with the locking sleeve 8, as a result of which the second engagement unit 11b is moved out of the engagement with the recess 8c, in particular toward the longitudinal axis L, so that the second spring 10 accelerates the displacement unit 11 against the discharge direction, i.e., in the proximal direction, so that, when the displacement unit 11 strikes against the signal abutment 12b, an acoustic and/or tactile signal is generated.

As can be seen best in FIG. 32a, the engagement of the second engagement element 6b of the retaining element 6 in the first recess 8b of the locking sleeve 8 continues to exist, as a result of which a movement of the locking sleeve 8 in the distal direction relative to the housing 2 is prevented.

By removing the autoinjector from the injection site, the second spring 10 can move the switching sleeve 15 and the needle protection sleeve 3 from the actuated position into the needle protection position by the needle protection stroke $H_N$, wherein the locking member 8a of the locking sleeve 8 is pressed out of the engagement with the recess 15a, wherein the switching sleeve 15 is moved relative to the locking sleeve 8 in the distal direction. When the needle protection sleeve 3 is in its needle protection position, the locking member 8a snaps into the switching sleeve 15, wherein the locking member 8a prevents the needle protection sleeve 3 from being pushed back into its actuated position. When an attempt is made to push the needle protection sleeve 3 from the needle protection position back into the actuated position, the switching member 15 strikes against the locking member 8a of the locking sleeve 8, which prevents the movement of the needle protection sleeve 3 into the actuated position. For this purpose, the locking sleeve 8 is braced axially against the start signal abutment of the dosing sleeve 5.

The invention claimed is:

1. An autoinjector device for administering a liquid product, in particular medication, the autoinjector comprising:
a housing;
a product container, at a distal end of which a needle is arranged and in which a piston is displaceably arranged, wherein the product container is retained in a product container holder;
a needle protection sleeve, which is displaceable from an initial position, in which a distal end of the needle protection sleeve is distally arranged beyond a needle tip of the needle, into the housing; and
a plunger rod arranged in the housing and displaceable by a preloaded discharge spring along a longitudinal axis in a distal direction, wherein, as a result of a displacement of the plunger rod in the distal direction, the piston is entrained by the plunger rod and displaces the product from the product container,
wherein when the needle protection sleeve is moved into the housing, the needle protection sleeve displaces a switching sleeve in the proximal direction from a position in which the switching sleeve prevents a first engagement element from being able to move out of a recess of the plunger rod into a release position in which the switching sleeve releases a movement of the first engagement element out of the recess of the plunger rod, whereby movement of the plunger rod in the distal direction is released, and
wherein as the switching sleeve moves in the proximal direction, the switching sleeve begins to abut against a locking sleeve to then entrain the locking sleeve such that the first engagement element is moved from the engagement with the recess of the plunger rod.

2. The autoinjector device of claim 1, further comprising a needle protection spring, wherein a proximal end of the needle protection spring acts on a displacement unit, and wherein a distal end of the needle protection spring acts, via the switching sleeve, on the needle protection sleeve.

3. The autoinjector device of claim 2, wherein the displacement unit forms an engagement unit that detachably engages in a recess of the plunger rod and blocks the plunger rod in a movement relative to the housing in the distal direction.

4. The autoinjector device of claim 1, wherein the product container holder is coupled to the housing in an axially fixed manner, wherein the needle protrudes beyond a distal end of the housing, and wherein the needle protection sleeve is displaceable from the initial position into the housing so that the needle protrudes from the distal end of the needle protection sleeve.

5. The autoinjector device of claim 1, further comprising a needle protection spring configured to move a displacement unit relative to the housing in a proximal direction, wherein: during the movement in the proximal direction, the displacement unit strikes against a fixed part of the device and thereby generates a tactile and/or acoustic signal, which signals a beginning of a discharge of a dose.

6. The autoinjector device of claim 1, wherein the switching sleeve moves in the proximal direction along the locking sleeve prior to abutting the locking sleeve.

7. The autoinjector device of claim 6, wherein the locking sleeve is shifted along the longitudinal axis by the switching sleeve in the proximal direction.

8. The autoinjector device of claim 1, wherein movement of the locking sleeve causes a first recess of the locking sleeve to be displaced along the longitudinal axis into a position of a second engagement element such that the first engagement element is moved from the engagement with the recess of the plunger rod.

9. An autoinjector device for administering a liquid product, in particular medication, the autoinjector comprising:
a housing;

a product container, at a distal end of which a needle is arranged and in which a piston is displaceably arranged, wherein the product container is retained in a product container holder;

a needle protection sleeve, which is displaceable from an initial position, in which a distal end of the needle protection sleeve is distally arranged beyond a needle tip of the needle, into the housing; and a plunger rod arranged in the housing and displaceable by a preloaded discharge spring along a longitudinal axis in a distal direction, wherein, as a result of a displacement of the plunger rod in the distal direction, the piston is entrained by the plunger rod and displaces the product from the product container, wherein when the needle protection sleeve is moved in the proximal direction into the housing, the needle protection sleeve displaces a switching sleeve from a position in which the switching sleeve prevents a first engagement element from being able to move out of a recess of the plunger rod into a release position in which the switching sleeve releases a movement of the first engagement element out of the recess of the plunger rod, whereby movement of the plunger rod in the distal direction is released, and wherein, during movement in the proximal direction, the switching sleeve abuts against a locking sleeve and entrains the locking sleeve to displace a first recess of the locking sleeve along the longitudinal axis into a position of a second engagement element, in order to release the engagement of the first engagement element from the recess of the plunger rod.

10. The autoinjector device of claim 9, further comprising a needle protection spring, wherein a proximal end of the needle protection spring acts on a displacement unit, and wherein a distal end of the needle protection spring acts, via the switching sleeve, on the needle protection sleeve.

11. The autoinjector device of claim 10, wherein the displacement unit forms an engagement unit that detachably engages in a recess of the plunger rod and blocks the plunger rod in a movement relative to the housing in the distal direction.

12. The autoinjector device of claim 9, wherein the product container holder is coupled to the housing in an axially fixed manner, wherein the needle protrudes beyond a distal end of the housing, and wherein the needle protection sleeve is displaceable from the initial position into the housing so that the needle protrudes from the distal end of the needle protection sleeve.

13. The autoinjector device of claim 9, further comprising a needle protection spring configured to move a displacement unit relative to the housing in a proximal direction, wherein: during the movement in the proximal direction, the displacement unit strikes against a fixed part of the device and thereby generates a tactile and/or acoustic signal, which signals a beginning of a discharge of a dose.

14. The autoinjector device of claim 9, wherein the switching sleeve moves in the proximal direction along the locking sleeve prior to abutting the locking sleeve.

15. The autoinjector device of claim 14, wherein the locking sleeve is shifted along the longitudinal axis by the switching sleeve in the proximal direction.

* * * * *